(12) United States Patent
Mirbagheri et al.

(10) Patent No.: US 12,213,754 B2
(45) Date of Patent: Feb. 4, 2025

(54) ROBOTIC SYSTEM FOR TELE-SURGERY

(71) Applicants: Alireza Mirbagheri, Tehran (IR);
Seyed Muhammad Yazdian, Tehran (IR); Farzam Farahmand, Tehran (IR); Saeed Sarkar, Tehran (IR); Mohammad Mehdi Moradi, Tehran (IR); Alireza Alamdar, Tehran (IR); Zahra Vosough, Tehran (IR); Sajad Molla Filabi, Tehran (IR); Pezhman Kheradmand, Tehran (IR); Faramarz Karimian, Tehran Tehran (IR); Karamollah Toolabi, Tehran (IR); Mohammad Reza Hanachi, Tehran (IR)

(72) Inventors: Alireza Mirbagheri, Tehran (IR);
Seyed Muhammad Yazdian, Tehran (IR); Farzam Farahmand, Tehran (IR); Saeed Sarkar, Tehran (IR); Mohammad Mehdi Moradi, Tehran (IR); Alireza Alamdar, Tehran (IR); Zahra Vosough, Tehran (IR); Sajad Molla Filabi, Tehran (IR); Pezhman Kheradmand, Tehran (IR); Faramarz Karimian, Tehran Tehran (IR); Karamollah Toolabi, Tehran (IR); Mohammad Reza Hanachi, Tehran (IR)

(73) Assignee: Sina Robotics and Medical Innovators Co. Ltd (IR)

( * ) Notice: Subject to any disclaimer, the term of this patent is extended or adjusted under 35 U.S.C. 154(b) by 221 days.

(21) Appl. No.: 18/091,291

(22) Filed: Dec. 29, 2022

(65) Prior Publication Data
US 2023/0147674 A1 May 11, 2023

Related U.S. Application Data

(63) Continuation-in-part of application No. 16/291,007, filed on Mar. 4, 2019, now Pat. No. 11,844,584, (Continued)

(51) Int. Cl.
*A61B 1/05* (2006.01)
*A61B 34/35* (2016.01)
(Continued)

(52) U.S. Cl.
CPC ............. *A61B 34/35* (2016.02); *A61B 34/37* (2016.02); *A61G 13/02* (2013.01); *A61G 13/04* (2013.01);
(Continued)

(58) Field of Classification Search
CPC ... A61B 34/35; A61B 34/37; A61B 2090/571; A61G 13/02; A61G 13/04; A61G 13/06; A61G 13/08
See application file for complete search history.

(56) References Cited

U.S. PATENT DOCUMENTS

| | | | |
|---|---|---|---|
| 2015/0119637 A1* | 4/2015 | Alvarez | A61B 1/00149 600/102 |
| 2019/0231460 A1* | 8/2019 | DiMaio | A61B 90/50 |

* cited by examiner

*Primary Examiner* — Muhammad S Islam

(57) ABSTRACT

An ergonomic adjustment mechanism comprising a vertical adjustment mechanism to move master robotic arms along a vertical axis. An exemplary vertical adjustment mechanism includes a main shaft extended along a horizontal axis between a first end and a second end, where the horizontal axis may be perpendicular to the vertical axis. The vertical adjustment mechanism further includes a linear actuator coupled to the horizontal beam to actuate a translational movement of the horizontal beam along the vertical axis. The ergonomic adjustment mechanism further includes a horizontal adjustment mechanism to move exemplary mas-
(Continued)

ter robotic arms along the horizontal axis. The horizontal adjustment mechanism includes a horizontal sliding rail that is mounted on the horizontal beam. Master robotic arms may be slidably mounted on the sliding rail, where the master robotic arms are slidable on the sliding rail along the horizontal axis.

16 Claims, 30 Drawing Sheets

Related U.S. Application Data which is a continuation of application No. 15/261,958, filed on Sep. 11, 2016, now Pat. No. 10,219,871.

(60) Provisional application No. 62/258,584, filed on Nov. 23, 2015.

(51) Int. Cl.
*A61B 34/37* (2016.01)
*A61G 13/02* (2006.01)
*A61G 13/04* (2006.01)
*A61G 13/06* (2006.01)
*A61G 13/08* (2006.01)
*A61B 90/57* (2016.01)

(52) U.S. Cl.
CPC ............ *A61G 13/06* (2013.01); *A61G 13/08* (2013.01); *A61B 2090/571* (2016.02)

ROBOTIC SYSTEM FOR TELE-SURGERY

CROSS-REFERENCE TO RELATED APPLICATION

This application is a continuation-in-part of U.S. patent application Ser. No. 16/291,007 filed Mar. 4, 2019, entitled "ROBOTIC SYSTEM FOR TELE-SURGERY," which is continuation of U.S. patent application Ser. No. 15/261,958 filed Sep. 11, 2016, entitled "A ROBOTIC SYSTEM FOR TELE-SURGERY," which takes priority from Provisional application No. 62/258,584, filed on Nov. 23, 2015, which are all hereby incorporated herein by reference in their entirety.

TECHNICAL FIELD

The present disclosure generally relates to surgical robotic systems and particularly to a robotic system for remote surgery. More particularly, the present disclosure is related to an ergonomic adjustment mechanism for a modular robotic system that may that allow a surgeon to perform a surgery in an ergonomic comfortable posture.

BACKGROUND

Minimally invasive surgery (MIS) is increasingly recognized as an effective alternative to traditional open surgery. MIS operations on the internal abdomen organs are performed as laparoscopic surgery, in which, a miniature video camera and long narrow surgical instruments are inserted into the abdomen cavity through small incisions. The camera provides an image of the interior of the abdomen, enabling the surgeon to explore the internal organs and perform the operation using the surgical instruments.

Laparoscopic surgery has advantages over open surgery. It causes less operative trauma and post-surgical complications that shorten the hospitalization time and associated costs. Also, it leads to a much faster recovery for a patient, which is of great physiological and psychological importance. However, it is technically more demanding and at the same time more tedious and difficult for the surgeon. Laparoscopic surgery usually takes longer and needs more concentration than an open surgery. In particular, during operation, surgeons hold postures that are more static and non-ergonomic compared to that of open surgery, likely caused by less efficient instruments. Static postures have been reported to impose more fatigue than dynamic ones because the muscles and tendons form lactic acid and toxins when held in static position. Moreover, the non-ergonomic postures may expose surgeons to physical discomfort that may reduce the surgeons' precision, dexterity and confidence during surgery.

With the advancements of the robotic surgery systems, the surgeons are now able to carry out MIS procedures remotely, in more ergonomic postures. Moreover, the rigid mechanical structure of robot, along with the more efficient high degree of freedom (DOF) surgical tools, allows for improved maneuverability and a more precise and stable surgery with less tremor. Such characteristics of the surgical robots have enabled successful surgeries for prostate cancer, bladder cancer, renal pelvis cancer, colon cancer, and the like.

A robotic surgery system consists of a master manipulator and a slave robot. As the surgeon operates the master manipulator, it generates and transmits control signals to the slave robot. Accordingly, the slave robot operates and performs surgery on the patient based on the received signals.

The currently available robotic surgery systems are based on integrated complex designs that require sophisticated infrastructure and educated human resources for maintenance and technical support. As a result, they are much expensive and involve very high maintenance costs. Moreover, the currently available systems utilize integrated and exclusively designed surgical tools at their end effector that are of single or limited use. Again, this increases their maintenance and operating costs considerably. Finally, the currently available systems do not provide force feedback information that is essential for avoiding excessive pinch or pull forces that could be damaging for the tissues under surgery.

In light of the above, it would be desirable to provide alternative designs and methodologies for robotic tele-surgery systems that improve the efficiency, flexibility, and comfort during surgery and reduce the price and operating and maintenance costs of the system. It would be particularly desirable to utilize modular designs that provide more configuration flexibility and the possibility of using conventional hand-held surgical tools. It would be further desirable to provide methods and techniques for measuring the tool-tissue force interactions to avoid large injurious forces on the tissues.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description and the drawings.

According to one or more exemplary embodiments, the present disclosure is directed to a robotic tele-surgery system, comprising a slave robotic arm comprising three degrees of freedom, the three degrees of freedom comprising at least one of grasp, roll, pitch, and yaw, a master robotic arm comprising six degrees of freedom, a controller configured to establish a master-slave relationship between the slave robotic arm and the master robotic arm, wherein movement at the master robotic arm produces a proportional movement in the slave robotic arm, and an ergonomic adjustment mechanism. In an exemplary embodiment, an ergonomic mechanism may comprise a vertical adjustment mechanism configured to move the master robotic arm along a vertical axis, the vertical adjustment mechanism comprising a horizontal beam extended along a horizontal axis between a first end and a second end, the horizontal axis perpendicular to the vertical axis, a linear actuator coupled to the horizontal beam, the linear actuator configured to actuate a translational movement of the horizontal beam along the vertical axis, and a horizontal adjustment mechanism configured to move the master robotic arm along the horizontal axis, the horizontal adjustment mechanism comprising a horizontal sliding rail mounted on the horizontal beam, the horizontal sliding rail parallel with the horizontal beam, wherein the master robotic arm slidably mounted on the sliding rail, the master robotic arm slidable on the sliding rail along the horizontal axis.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for illustration and description only and are not intended as a definition of the limits of the present disclosure. Embodiments of the present disclosure will now be described by way of example in association with the accompanying drawings, in which.

DETAILED DESCRIPTION

The novel features which are believed to be characteristic of the present disclosure, as to its structure, organization, use and method of operation, together with further objectives and advantages thereof, will be better understood from the following discussion.

Disclosed exemplary systems and methods directed to laparoscopic tele-surgery may include a modular robotic tele-surgery system comprising a surgeon-side unit and a patient-side unit. The surgeon-side unit may include different assemblies to enable a user (i.e., a surgeon) to perform a tele-surgery. The hand movements of the surgeon may be captured in the surgeon-side unit and they may be reconstructed in the patient-side unit to enable the surgeon to remotely perform a laparoscopic surgery. Moreover, the force and torque exerted on the surgical tools at the surgery site may be sent to the surgeon-side unit as a haptic feedback to the hands of the surgeon. The patient-side unit may include slave robotic arms that may be mounted and adjusted on a patient support assembly using passive mounting mechanisms. The orientation of the patient during surgery may be adjusted by the patient support assembly and the fixed point of the robotic arms may be aligned with the incision location utilizing the passive mounting mechanisms that are mounted on the patient support assembly. Benefits of these features may include, but are not limited to, maintaining the alignment between the fixed point of the slave robotic arms and the incision location during surgery, and enabling changes in the patient's orientation during surgery without the need for removing surgical instruments from the patient's body. Moreover, the surgeon-side unit may include adjustment mechanisms that enable the surgeon to perform the surgery in an ergonomic comfortable posture, in either a sitting position or a standing position.

Figure 1A:
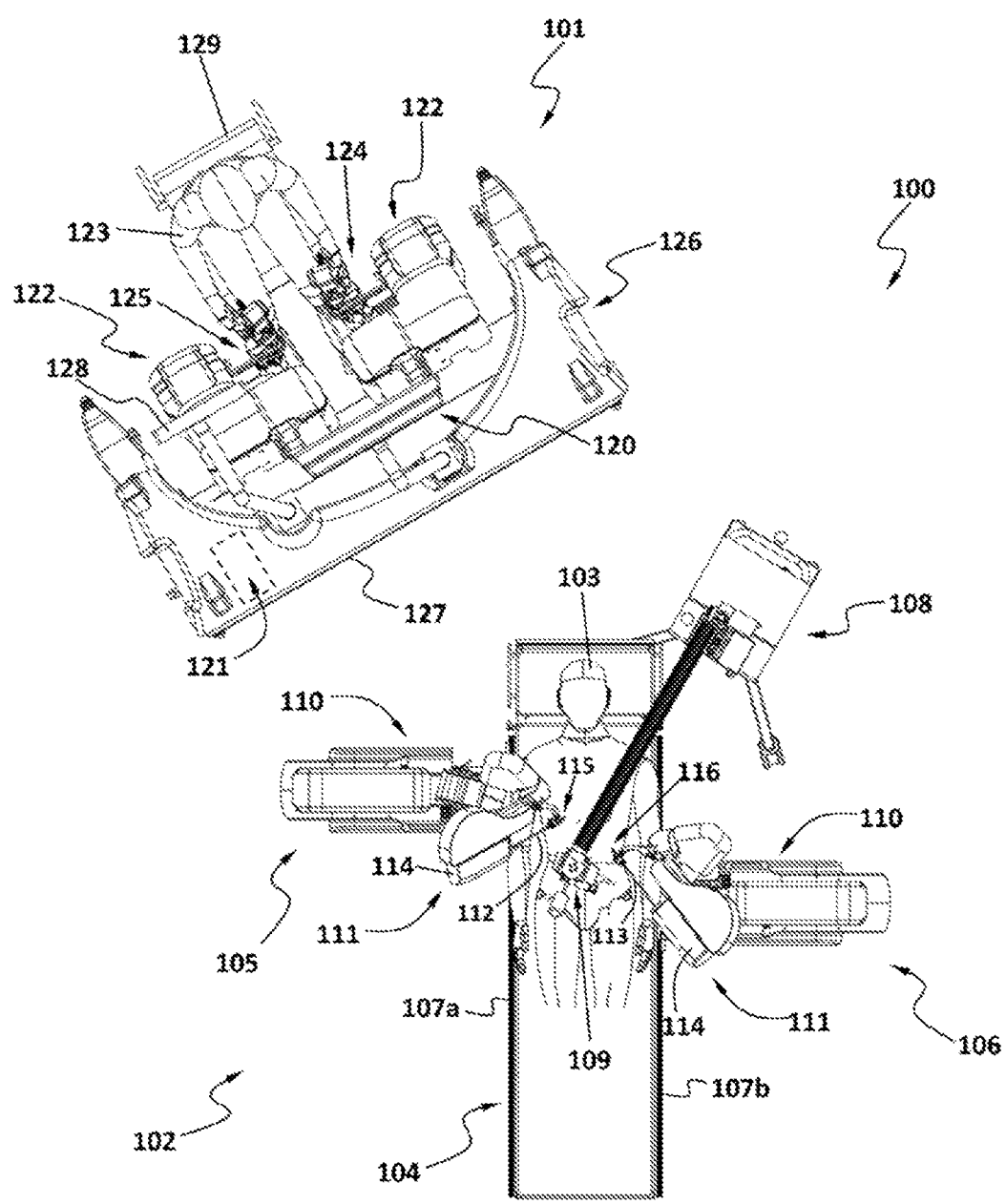
FIG. 1A illustrates a top view of one example implementation of a robotic tele-surgery system, consistent with one or more exemplary embodiments of the present disclosure.

FIG. 1A is a top view of one example robotic tele-surgery system 100 in accordance with one or more aspects of the present disclosure. The robotic tele-surgery system 100 may include a surgeon-side unit 101 and a patient-side unit 102 that may be in a master-slave relationship with one another, which will be described in detail later in the present disclosure.

Referring to FIG. 1A, the robotic tele-surgery system 100 may be configured for performing minimally invasive surgeries. The system 100 may be used to perform a surgical procedure on a patient 103 that is typically lying on a patient support assembly (e.g., operating table, etc.) 104. Mounted to the patient support assembly 104 is a first arm assembly 105, and a second arm assembly 106. The arm assemblies 105 and 106 may be mounted to the table so that the arms 105 and 106 are in a plane proximate to patient 103 and movable with patient support assembly 105. Moreover, arms 105 and 106 may be slidably mounted on track assemblies 107a and 107b on either side of the patient support assembly 104 and they may be configured to be slidably movable along the sides of the patient support assembly 104. The system may include an endoscope/camera assembly 108 that may be configured to hold and position an endoscope/camera 109.

The first and second arm assemblies 105 and 106 each may be configured with a passive mounting mechanism 110 and a slave robotic arm 111 that is mounted on and extending from the passive mounting mechanism 110. Surgical instruments 112 and 113 may be removably coupled at the end of each slave robotic arm 111 of the first and second arm assemblies 105, 106. Each of the instruments 112, 113 may be coupled to a corresponding slave robotic arm 111 in a variety of fashions, for example, using a tool adapting mechanism 114. The tool adapting mechanism 114 may be a mechanical or specifically a servo-mechanical interface that may be configured for manipulating end effectors 115 and 116 of the surgical instruments 112 and 113. The tool adapting mechanism 114 may include a plurality of motion and electrical feed-throughs for articulating the instruments, and for sending electrical signals to and from the instrument, e.g., force and torque feedback signals, etc. The tool adapting mechanism 114 may be configured for coupling the distal end of the slave robotic arms 111 with the surgical instruments 112, 113 and transferring at least two DOFs from the arms 111 to the instruments 112 and 113.

According to some implementations, the surgical instrument 112 and 113 may be non-articulating laparoscopic instruments, handled wrist-articulating instruments, or handle-free wrist articulating instruments having at least two degrees of freedom of grasp, roll, pitch, and yaw.

The passive mounting mechanism 110 may be configured with three Degrees of Freedom (DOFs) and may be configured for aligning the fixed point of the slave robotic arms 111 with the incision location prior to the surgery. The slave robotic arms 111 may be configured with three active DOFs and one passive DOF and they may be configured to manipulate the instruments 112, 113.

Figure 1B:
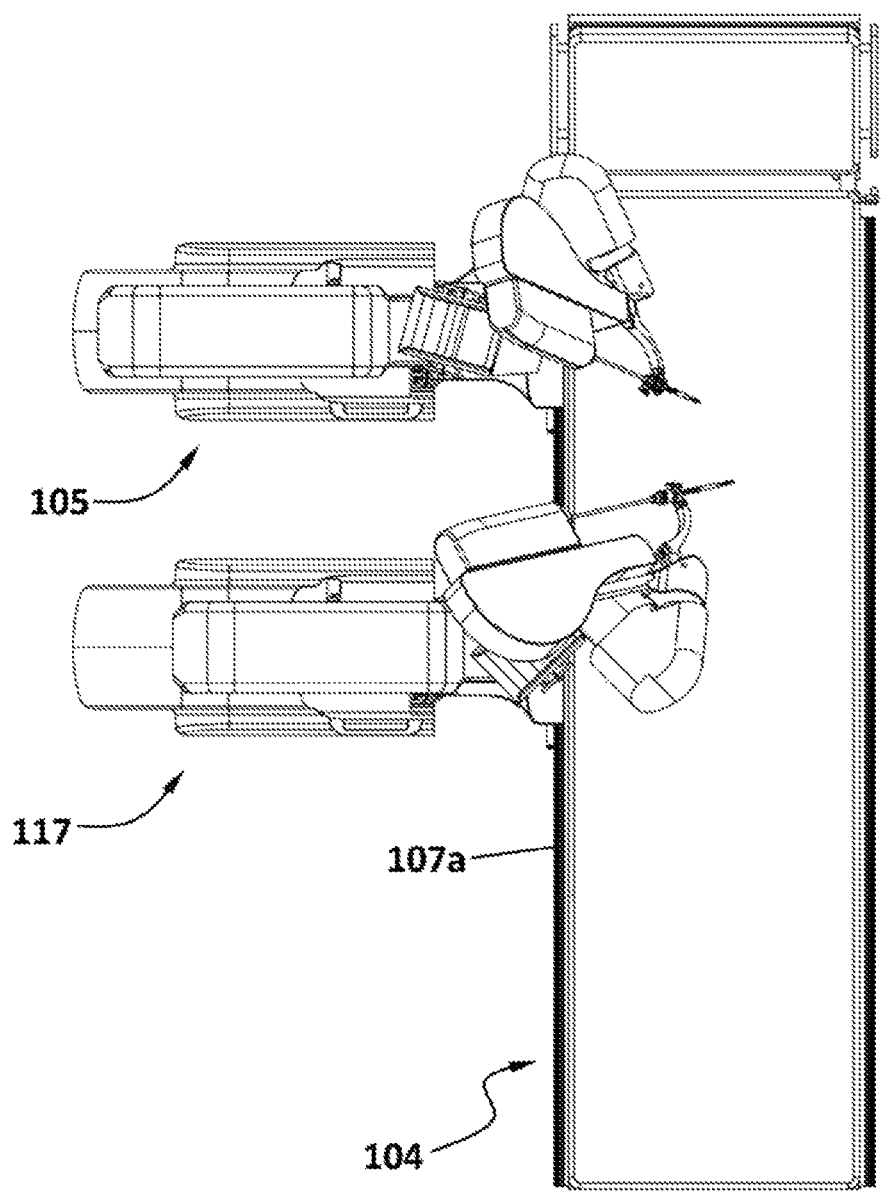
FIG. 1B illustrates an example configuration of arm assemblies with two arms, consistent with one or more exemplary embodiments of the present disclosure.
Figure 1C:
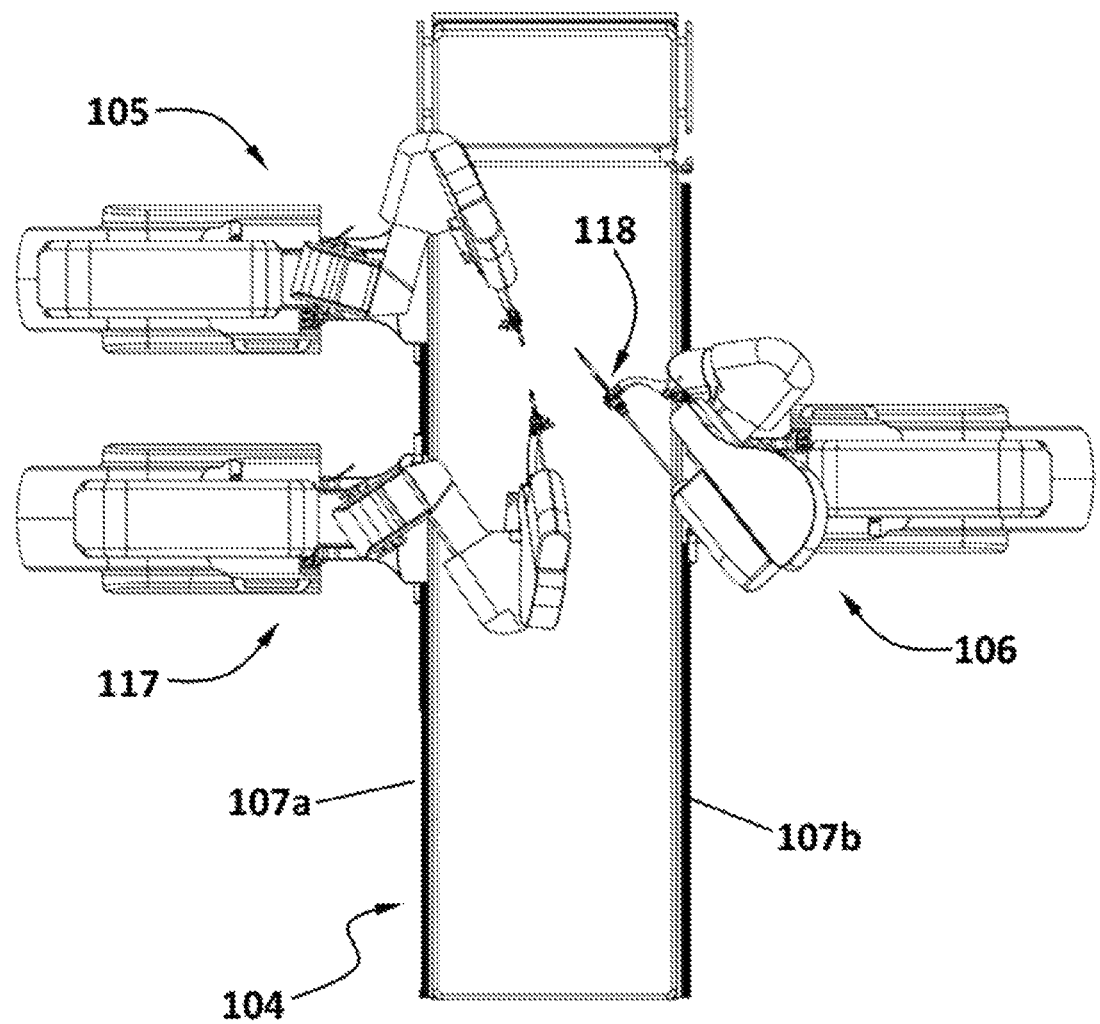
FIG. 1C illustrates an example configuration of arm assemblies with three arms, consistent with one or more exemplary embodiments of the present disclosure.
Figure 1D:
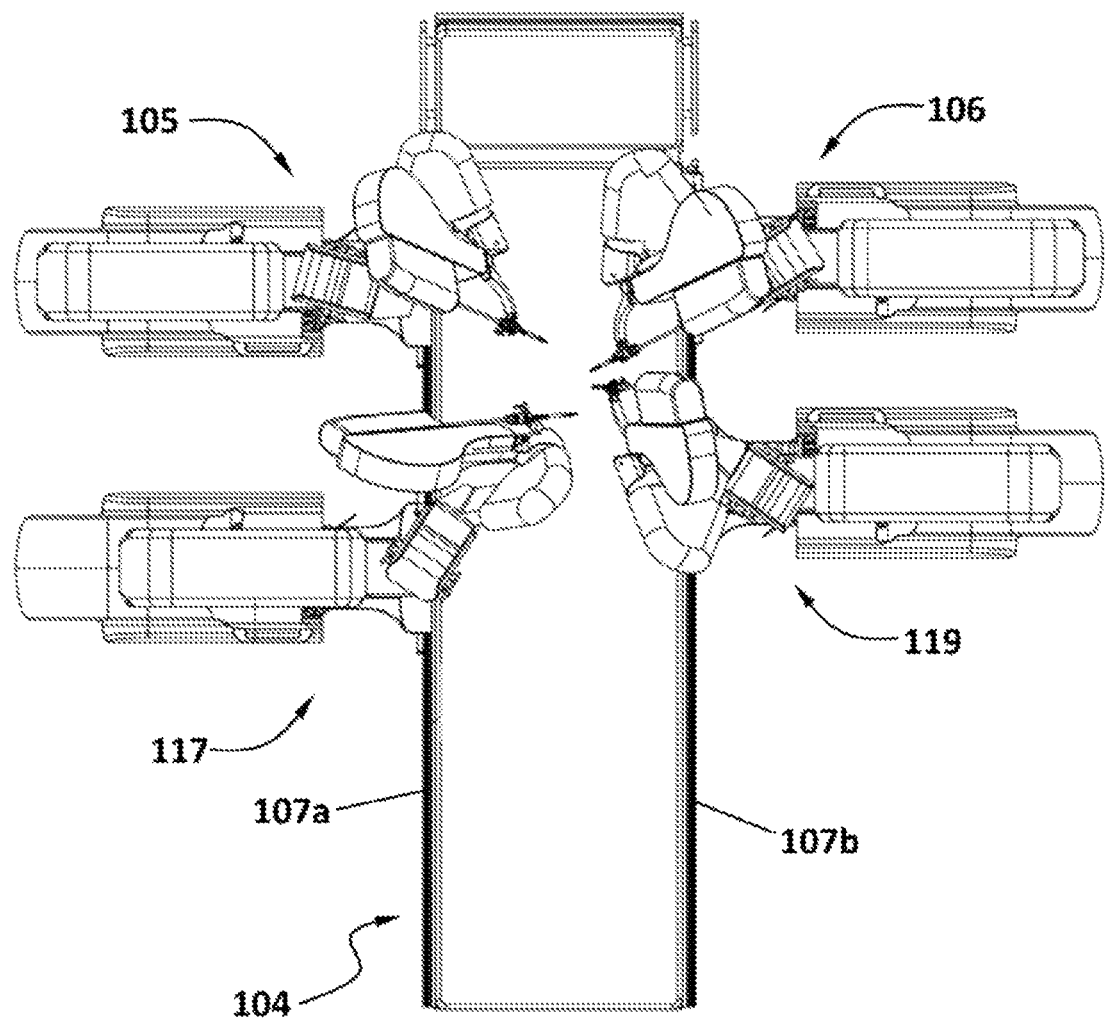
FIG. 1D illustrates an example configuration of arm assemblies with four arms, consistent with one or more exemplary embodiments of the present disclosure.

Referring to FIGS. 1B-1D, it is to be understood that the tele-surgery system may have any number of arm assemblies. FIG. 1B shows an example implementation with two arm assemblies 105 and 117 slidably mounted on the track assembly 107 a on the side of the patient support assembly 104. In this exemplary configuration, the two arm assemblies 105 and 117 may be mounted on one side of the patient support assembly 104 and the other side may be left empty, for example, for an assistant to be able to take part in the surgery.

FIG. 1C shows an example implementation with three arm assemblies 105, 106, and 117 slidably mounted on the sliding tracks 107 a and 107 b on either side of the patient support assembly 104. The additional arm assembly 106, may hold an additional instrument 118.

FIG. 1D shows an example implementation with four arm assemblies 105, 106, 117, and 119 slidably mounted on the sliding tracks 107a and 107b on either side of the patient support assembly 104. In an implementation, one of the arm assemblies 105, 106, 117, or 119 may be configured with an endoscope or camera (not visible in FIGS. 1A-1D) that is attached to its slave robotic arm (not explicitly numbered in FIG. 1D) and that arm assembly may be called an endoscope/camera arm. However, it is to be appreciated that the configuration of the endoscope/camera arm, may be different as the purpose of the endoscope/camera arm is to hold and position an endoscope or camera as opposed to hold and position a surgical instrument.

Referring to FIG. 1A, the instruments 112 and 113 and the endoscope/camera 109 may be inserted through incisions cut into the skin of the patient 103. The endoscope/camera 109 may be coupled to a monitor 120 which displays images of the internal organs of the patient 103. The slave robotic arms 111 as well as the endoscope/camera assembly 108 may be coupled to a controller 121 which may control the movement of the arms 111 and the endoscope/camera assembly 108. The arms 111 may be coupled to the controller 121 via wiring, cabling, or via a transmitter/receiver system such that control signals may be passed from the controller 121 to each of the arms 111.

The controller 121 receives the input signals from master robotic arms 122 and moves the slave robotic arms 111 of the arm assemblies 105 and 106 in accordance with the input commands of a surgeon 123.

The movement and positioning of instruments 112, 113 attached to the slave robotic arms 111 of the first and second arm assemblies 105 and 106 may be controlled by the surgeon 123 at a pair of master handles 124 and 125. Each of the master handles 124, 125 which may be manipulated by the surgeon 123, has a master-slave relationship with a corresponding one of the slave robotic arms 111 so that movement of a handle 124 or 125 produces a corresponding movement of the surgical instrument 112, 113 attached to the slave robotic arms 111.

The master handles 124 and 125 that are a part of the master robotic arms 122 may be mounted to an ergonomic adjustment mechanism 126 of a surgeon console 127. A second monitor 128 may be mounted onto the surgeon console 127 and be configured to function as a user interface unit. The master handles 124 and 125 are also coupled to the controller 121. The controller 121 receives input signals from the master handles 124 and 125, computes a corresponding movement of the surgical instruments 112, 113, and provides output signals to move the slave robotic arms 111 and the instruments 112 and 113. The master robotic arms 122 may be configured to provide a plurality of DOFs to the arm assemblies 105 and 106 and corresponding surgical instruments 112 and 113, the DOFs may include pitch and yaw movements of the instruments 112 and 113, rotational and axial movements, and articulation of the end effectors 115 and 116 on the instruments 112 and 113.

The ergonomic adjustment mechanism 126 may be configured with three passive DOFs to allow for adjustment of the position and orientation of the master robotic arms 122 in order to enable the surgeon 123 to perform the surgery in an ergonomic comfortable posture, in either a sitting position or a standing position. A chair 129 may be provided for the sitting position. The ergonomic adjustment mechanism 126 will be described in detail later in the present disclosure.

The orientation of the patient 103 during surgery may be adjusted by the patient support assembly 104 and the fixed point of the slave robotic arms 111 may be aligned with the incision location utilizing the passive mounting mechanisms 110 that are mounted on the patient support assembly 104. Benefits of these features may include, but are not limited to, maintaining the alignment between the fixed point of the slave robotic arms 111 and the incision location during surgery, and enabling changes in the patient's orientation during surgery without the need for removing surgical instruments 112 and 113 from the patient's body. The patient 103 alignment may be desirable for certain surgeries to position internal organs by gravity effects.

Patient-Side Unit

Figure 2A:
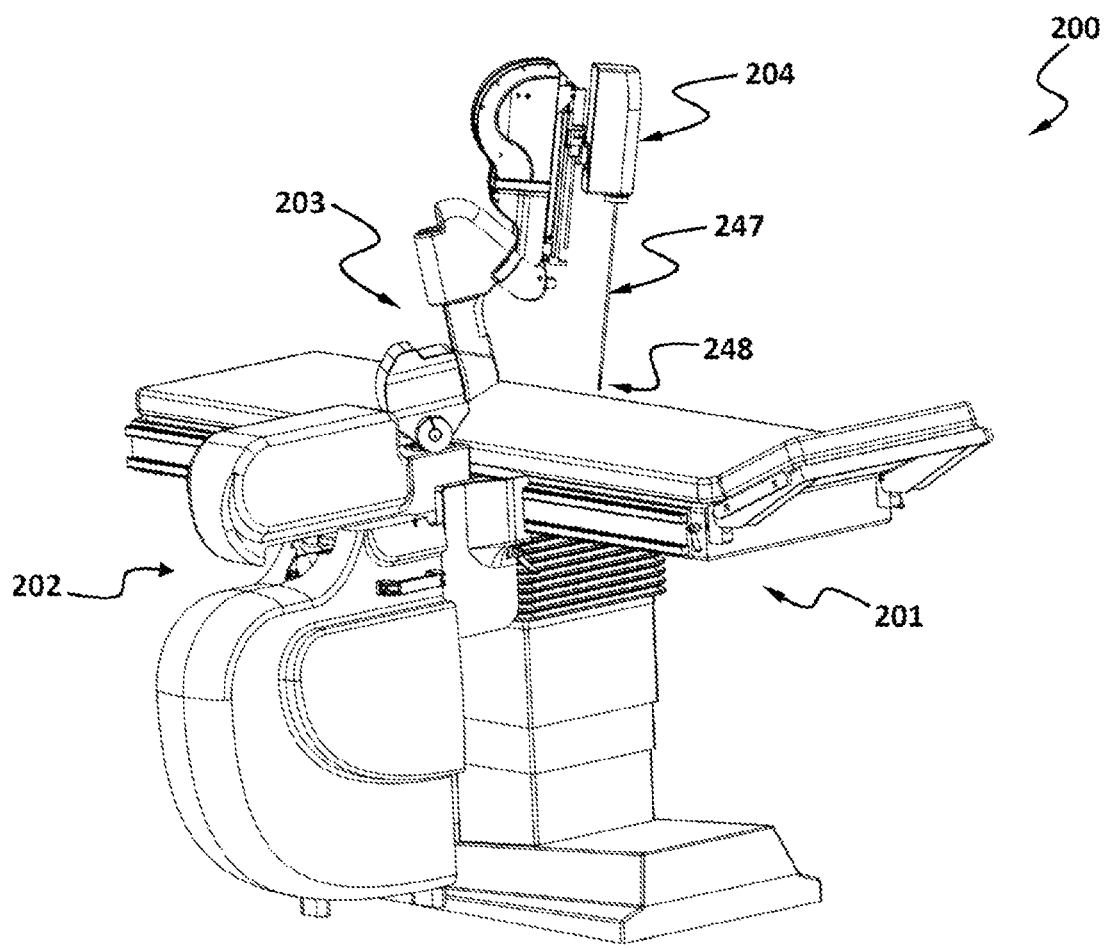
FIG. 2A illustrates one implementation of an example patient-side unit for one robotic tele-surgery system, consistent with one or more exemplary embodiments of the present disclosure.
Figure 2B:
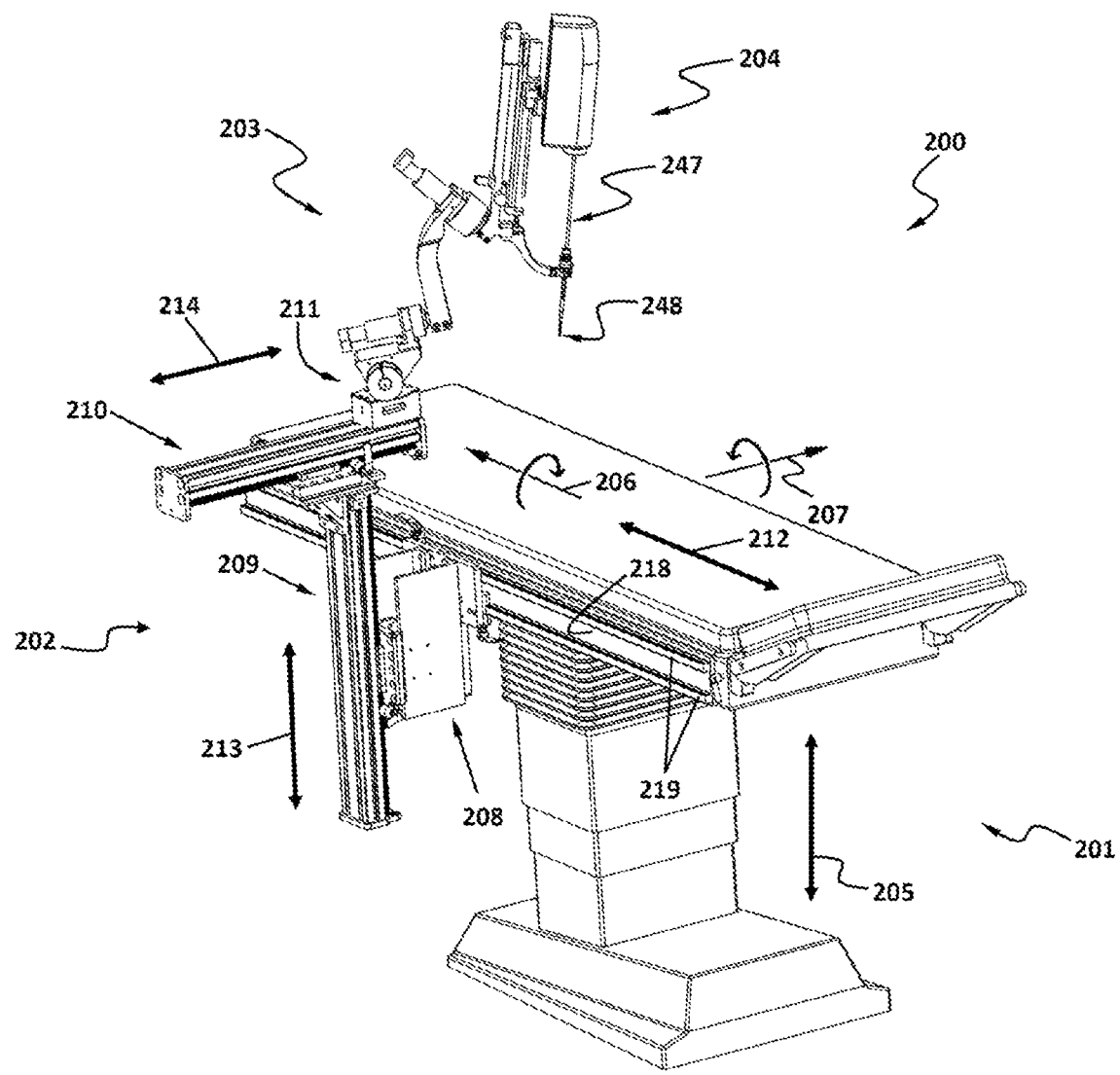
FIG. 2B illustrates one implementation of an example patient-side unit without protective covers, consistent with one or more exemplary embodiments of the present disclosure.

FIG. 2A shows a perspective view of one example patient-side unit 200. FIG. 2B shows a perspective view of the patient-side unit 200 without protective covers. Referring to FIG. 2A, the patient-side unit 200 may include a patient support assembly 201, a passive mounting mechanism 202, a slave robotic arm 203, and a tool adapting mechanism 204 that is mounted on distal end of the slave robotic arm 203. The tool adapting mechanism 204 may be configured for coupling the distal end of the slave robotic arm 203 with a surgical instrument 247 having an end-effector 248 and transferring at least two DOFs from the arm 203 to the end-effector 248.

Referring to FIG. 2B, the patient support assembly 201, may be structured as a bed or a treatment table, configured to support a patient during surgery. The patient support assembly 201 may be configured with three DOFs (i.e., a linear DOF and two rotational DOFs). The linear DOF may include a substantially vertical axis 205 and the two rotational DOFs may include a roll axis 206 and a pitch axis 207. The aforementioned DOFs may allow for changing the height of the patient support assembly 201 and the orientation of the patient's body during surgery. The patient support assembly 202 may include a moving mechanism to effectuate translational movements of the patient support assembly 202 along axis 205 and rotational movements of the patient support assembly 202 about axes 206 and 207.

Referring to FIGS. 2B-2E, the passive mounting mechanism 202 may be configured to allow for mounting the slave robotic arm 203 on the side of the patient support assembly 201. The passive mounting mechanism 202 may include a first sliding segment 208, a second sliding segment 209, a third sliding segment 210, and a pan/tilt mounting mechanism 211. The first sliding segment 208 may be slidably mounted on the patient support assembly 201 and it may be configured to allow for a sliding movement of the passive mounting assembly 202 along a first linear axis 212 of the patient support assembly 201. The second sliding segment 209 may be slidably mounted on the first sliding segment 208 and it may be configured to allow for a sliding movement of the second sliding assembly 209 along a second linear axis 213. The third sliding segment 210 may be slidably mounted on the second sliding segment 209 and it may be configured to allow for a sliding movement of the third sliding assembly 210 along a third linear axis 214. The pan/tilt mounting mechanism 211 may be mounted on the third sliding segment 210 and it may be configured to allow for mounting the slave robotic arm 203 on the passive mounting mechanism 202.

Figure 2C:
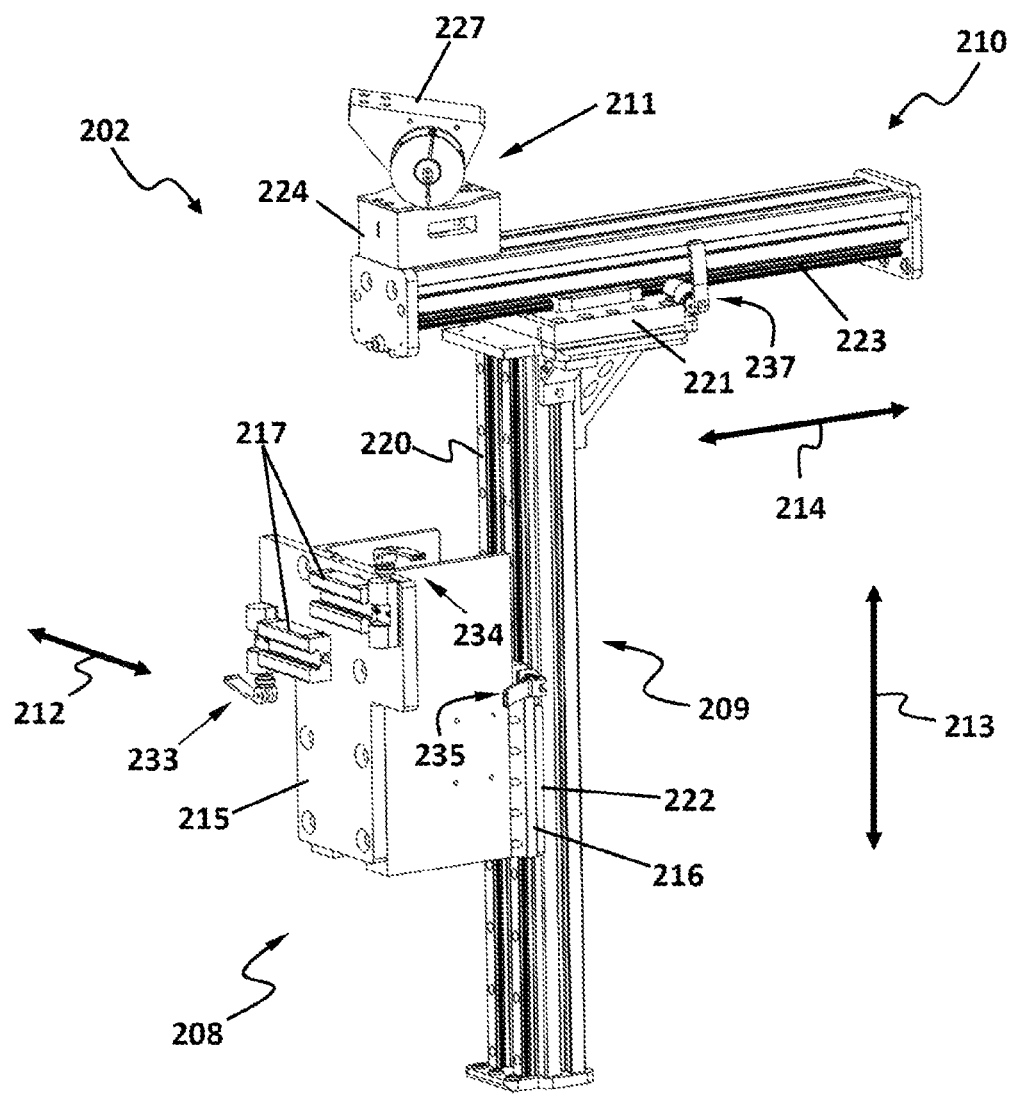
FIG. 2C is an assembled view of one implementation of an example passive mounting mechanism for a robotic tele-surgery system, consistent with one or more exemplary embodiments of the present disclosure.
Figure 2D:
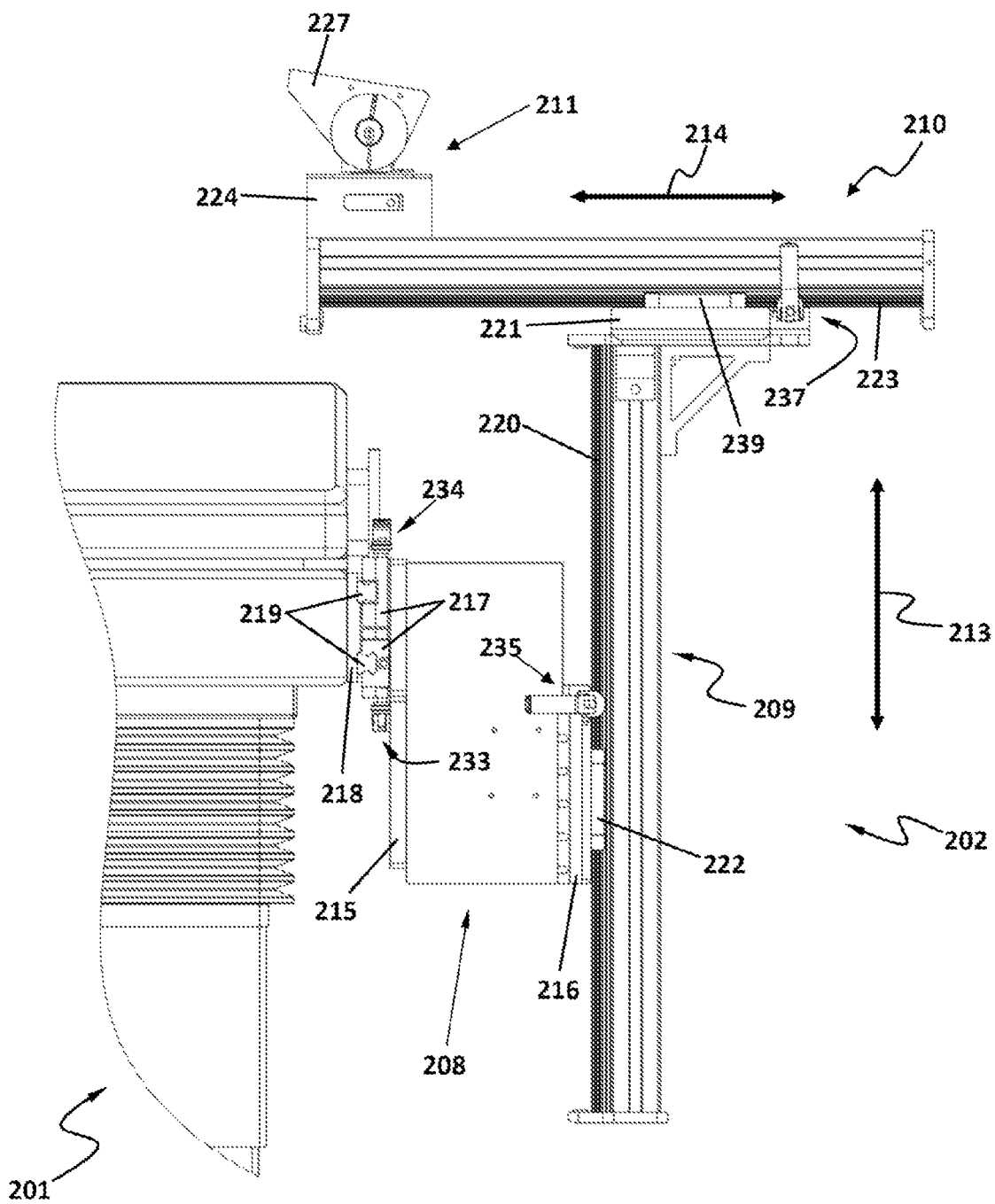
FIG. 2D is a left view of one implementation of an example passive mounting mechanism for a robotic tele-surgery system, consistent with one or more exemplary embodiments of the present disclosure.
Figure 2E:
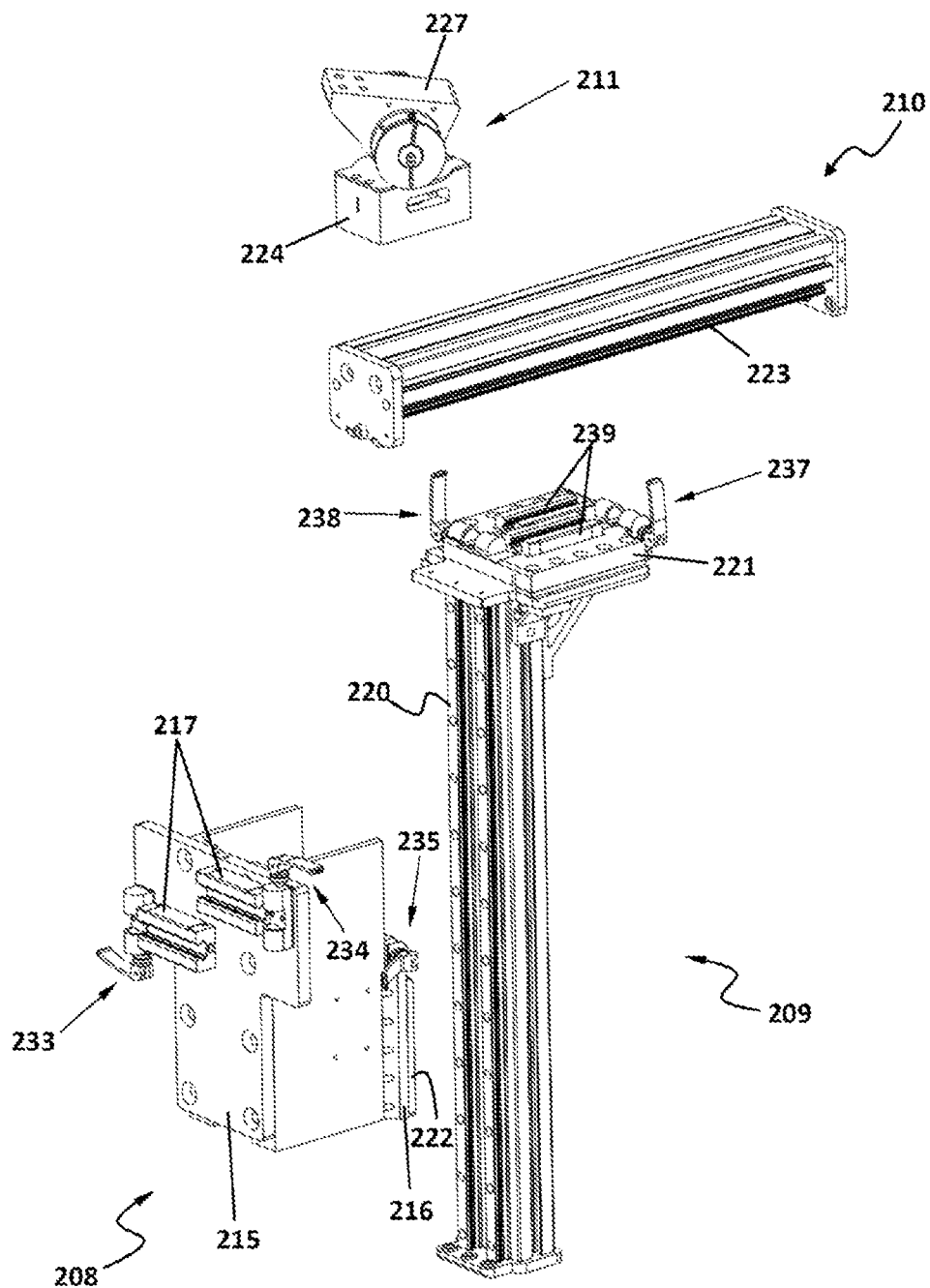
FIG. 2E illustrates an exploded view of one implementation of an example passive mounting mechanism for a robotic tele-surgery system, consistent with one or more exemplary embodiments of the present disclosure.

Referring to FIGS. 2C-2E, the first sliding segment 208 may include a first wagon assembly 215 and a second wagon assembly 216. The first wagon assembly 215 may be configured to allow for slidably mounting the first sliding segment 208 on the patient support assembly 201 and the second wagon assembly 216 may be configured to allow for slidably mounting the second sliding segment 209 on the first sliding segment 208.

Referring to FIG. 2D, the first wagon assembly 215 may include first sliding wagons 217 that may be slidably mounted on a bed track assembly 218 that may be attached to the side of the patient support assembly 201. The bed track assembly 218, may include two parallel rails 219. The first sliding wagons 217 may be slidably mounted on the two parallel rails 219 and may be slidably movable on the two parallel rails 219 along the first linear axis 212 (visible and numbered in FIGS. 2B and 2C).

Referring to FIGS. 2C-2E, the second sliding segment 209 may include a first track assembly 220, and a third wagon assembly 221. The second sliding segment 209 is mounted on the first sliding segment 208 via the second wagon assembly 216 of the first sliding segment 208. Referring to FIGS. 2D and 2G, the second wagon assembly 216 may include second sliding wagons 222 that may be slidably coupled with the first track assembly 220 of the second sliding segment 209 and the second sliding wagons 222 may be slidably movable on the first track assembly 220 along the second linear axis 213.

Referring to FIGS. 2C-2E, the third sliding segment 210 may include a second track assembly 223. The second track assembly 223 may be slidably coupled with the third wagon assembly 221 of the second sliding segment 209 and it may be configured to allow for a sliding movement of the third sliding segment 210 relative to the second sliding segment 209 along the third linear axis 214.

Figure 2F:
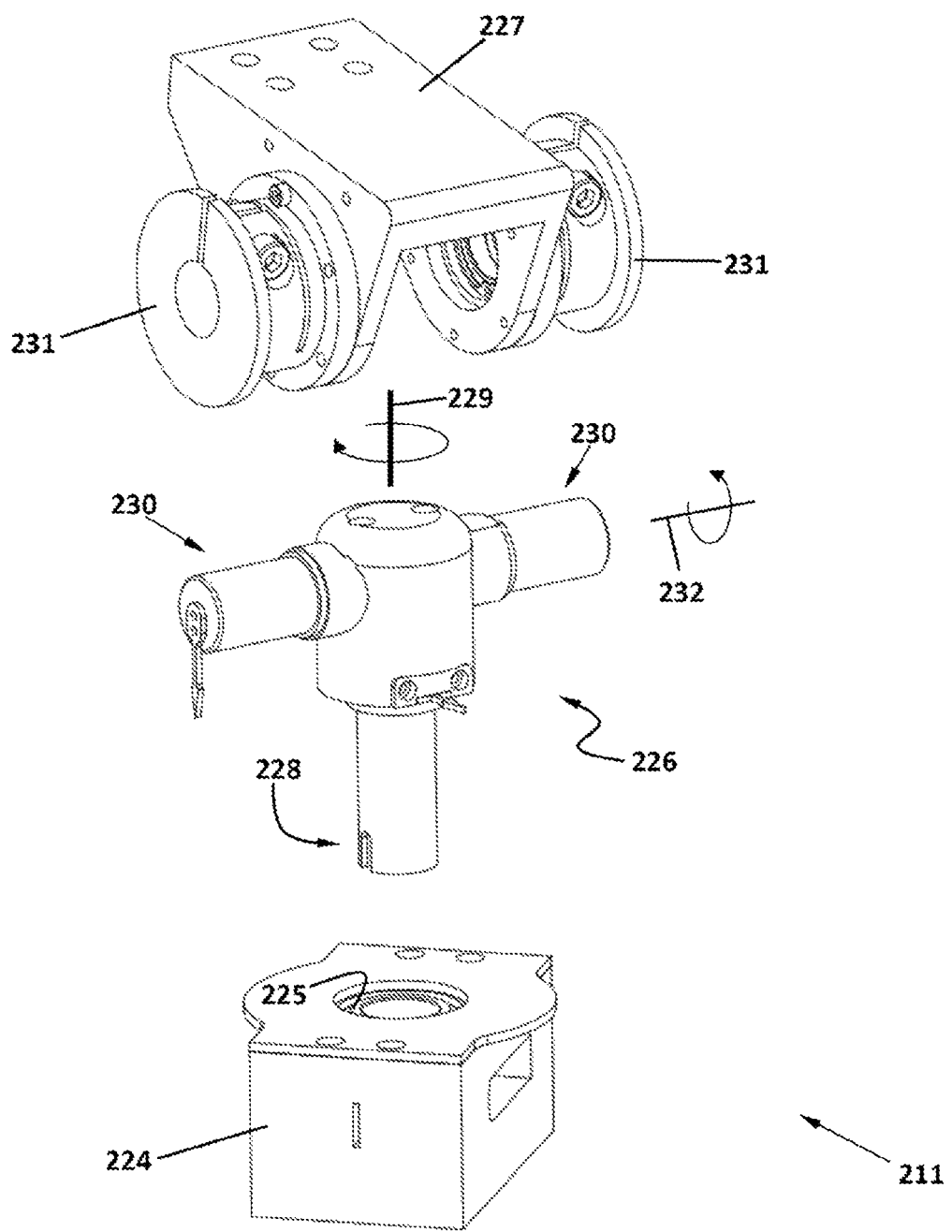
FIG. 2F illustrates an exploded view of one implementation of an example pan/tilt mounting mechanism for a robotic tele-surgery system, consistent with one or more exemplary embodiments of the present disclosure.
Figure 2G:
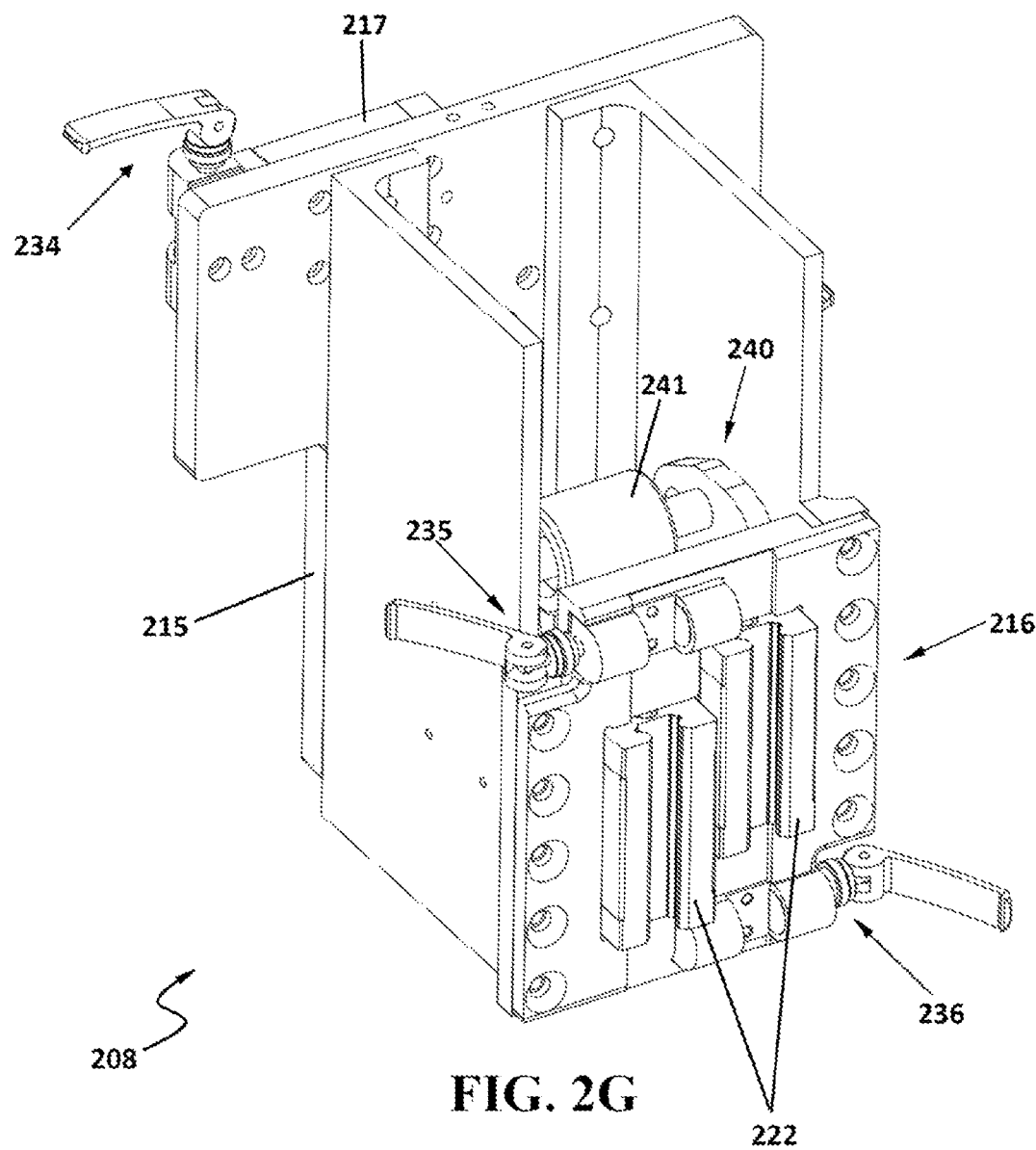
FIG. 2G illustrates one implementation of an example first sliding segment for a robotic tele-surgery system, consistent with one or more exemplary embodiments of the present disclosure.

Referring to FIGS. 2C-2F, the pan/tilt mounting mechanism 211 may be mounted on the third sliding segment 210 via a first attachment member 224. Referring to FIG. 2F, the pan/tilt mechanism 211 may include: a bearing unit 225 housed in the first attachment member 224; a shaft assembly 226; and an arm attachment interface 227. Lower end 228 of the shaft assembly 226 may be coupled with the bearing unit 225. The bearing unit 225 may be configured to facilitate a pan rotational movement of the pan/tilt mounting mechanism 211 about a pan axis 229. Two upper ends 230 of the shaft assembly 235 may be coupled with the arm attachment interface 227 via two tilt bearing units 231 attached to either sides of the arm attachment interface 227 that are configured to facilitate a tilt rotational movement of the pan/tilt mounting mechanism 211 about a tilt axis 232. Referring to FIGS. 2A and 2F, the slave robotic arm 203 may be mounted on the passive mounting mechanism 202 via the arm attachment interface 227. The pan/tilt mounting mechanism 211 may be configured to allow for rotational movements of the slave robotic arm 203 about the pan axis 229 and the tilt axis 232.

Referring to FIGS. 2B and 2F, the five DOFs (i.e., three translational DOFs along axes 212, 213, 214, and two pan and tilt DOFs about axes 229 and 232) of the passive mounting mechanism 202 may be locked in position before surgery. Referring to FIGS. 2C-2E, the first wagon assembly 215 may include two locks 233 and 234 that may be configured for locking the first sliding wagons 217 in position. Referring to FIG. 2G, the second wagon assembly 216 may include two locks 235 and 236 that may be configured for locking the second sliding wagons 222 in position. Referring to FIG. 2E, the third wagon assembly 221 may include two locks 237 and 238 that may be configured for locking sliding wagons 239 of the third wagon assembly 221 in position.

Referring to FIGS. 2C and 2G, the first sliding segment 208 may further include a first counter weight mechanism 240 that may be configured to facilitate the translational movement of the second sliding member 209 along the axis 213. The first counter weight mechanism 240 may be configured to compensate for the weight of the second sliding segment 209, third sliding segment 210, pan/tilt mounting mechanism 211, and the slave robotic arm 203 and as a result, it may facilitate manual lifting of the second sliding segment 209 along axis 213. The first counter weight mechanism 240 may include, for example a first constant-force spring 241.

Figure 2H:
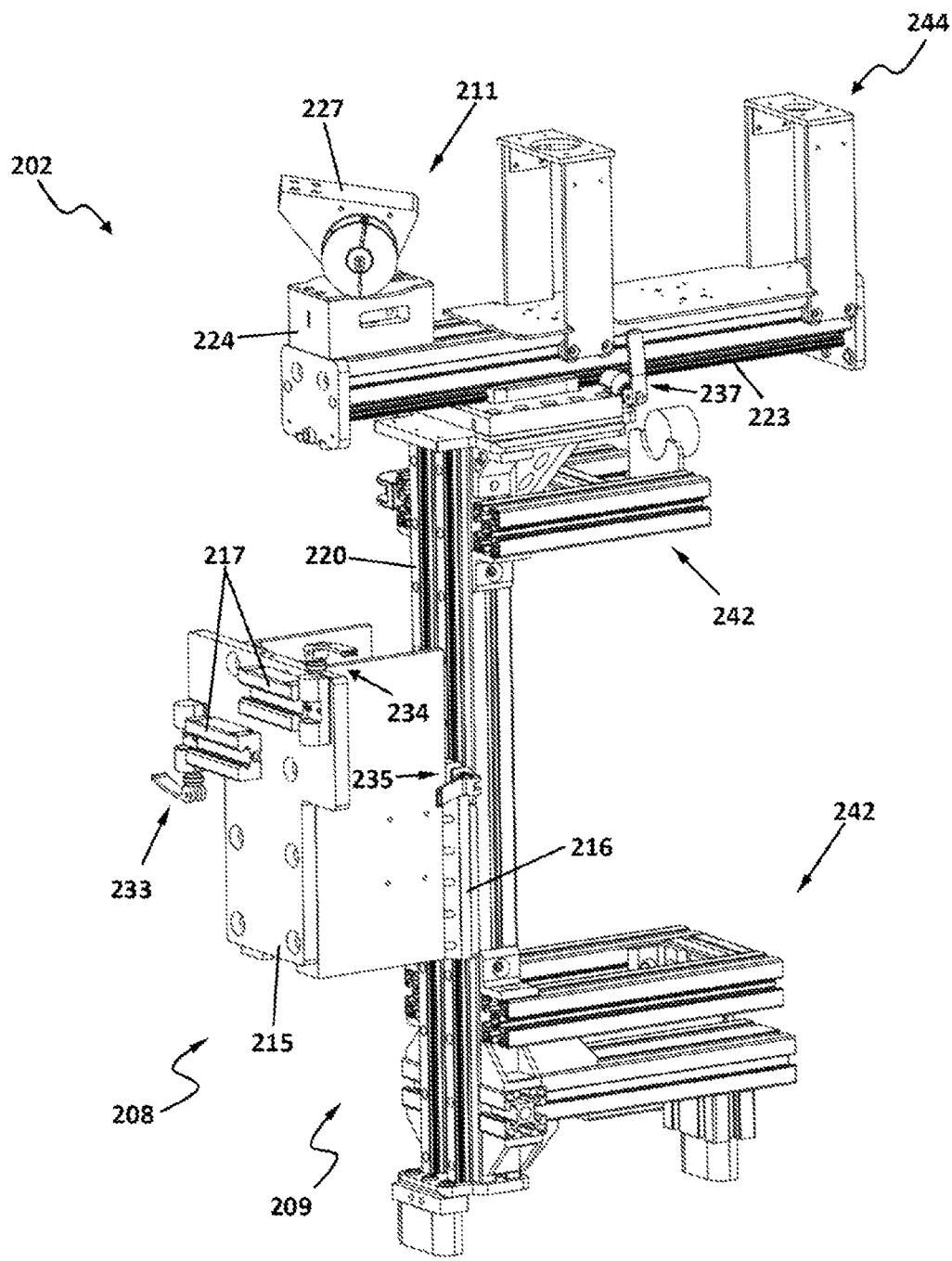
FIG. 2H is an assembled view of one implementation of an example passive mounting mechanism with support structures for a robotic tele-surgery system, consistent with one or more exemplary embodiments of the present disclosure.
Figure 2I:
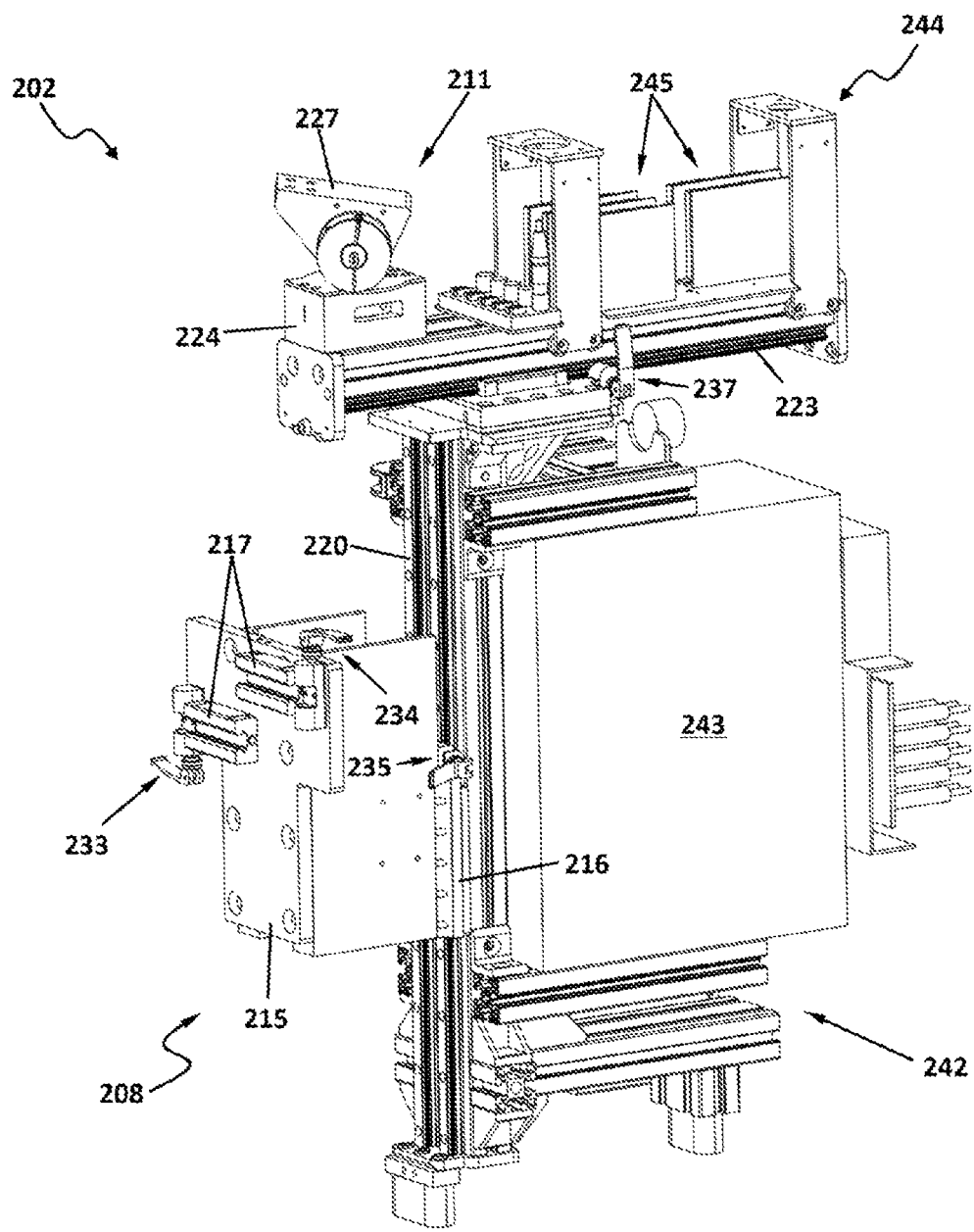
FIG. 2I is an assembled view of one implementation of an example passive mounting mechanism with support structures for controller components and motor drivers for a robotic tele-surgery system, consistent with one or more exemplary embodiments of the present disclosure.

Referring to FIGS. 2H and 2I, the second sliding segment 209 may further include a second support structure 242 that may be configured for supporting various electronic parts, for example, controller components 243, which form a part of the controller. The third sliding segment 210 may further include a third support structure 244 that may be configured for supporting various electronic parts, for example, motor drivers 245.

Figure 3A:
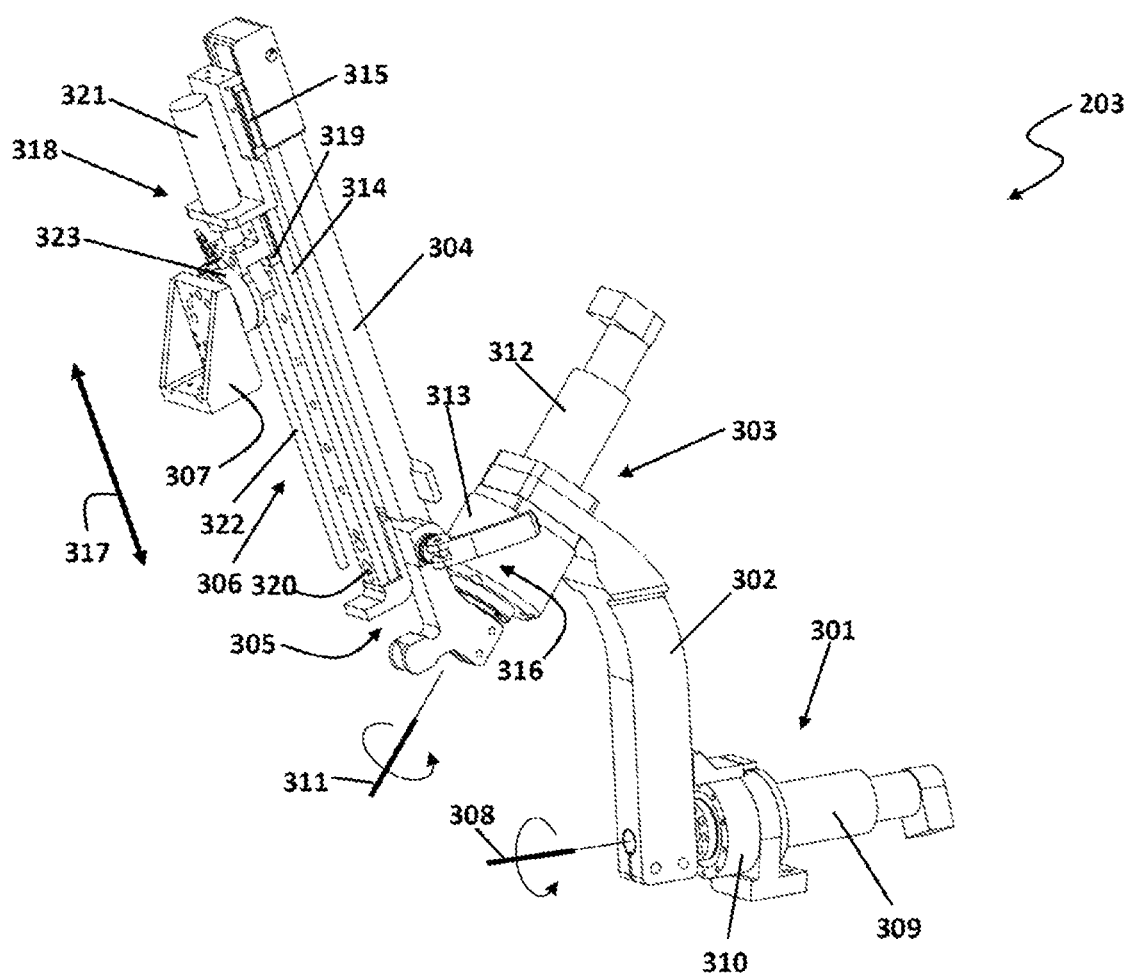
FIG. 3A is an assembled view of one implementation of an example slave robotic arm for a robotic tele-surgery system, consistent with one or more exemplary embodiments of the present disclosure.
Figure 3B:
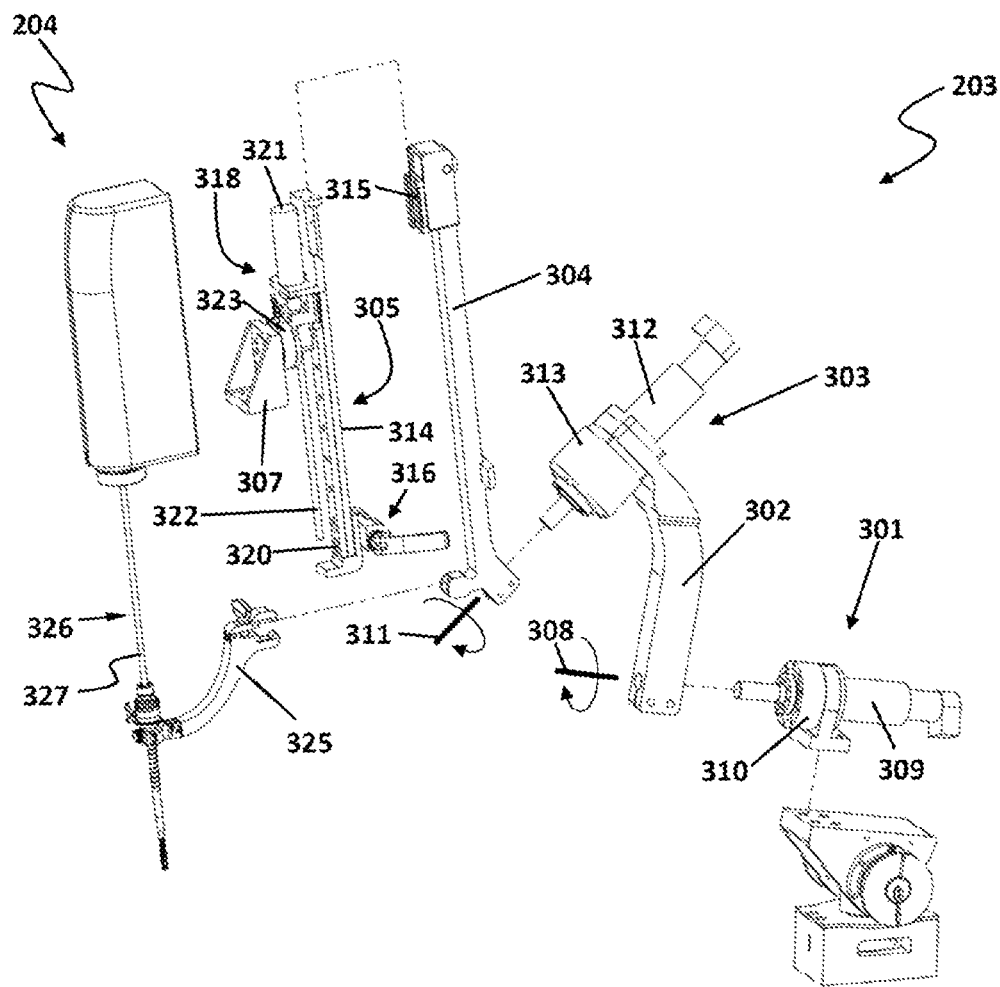
FIG. 3B illustrates an exploded view of one implementation of an example slave robotic arm for a robotic tele-surgery system, consistent with one or more exemplary embodiments of the present disclosure.
Figure 3C:
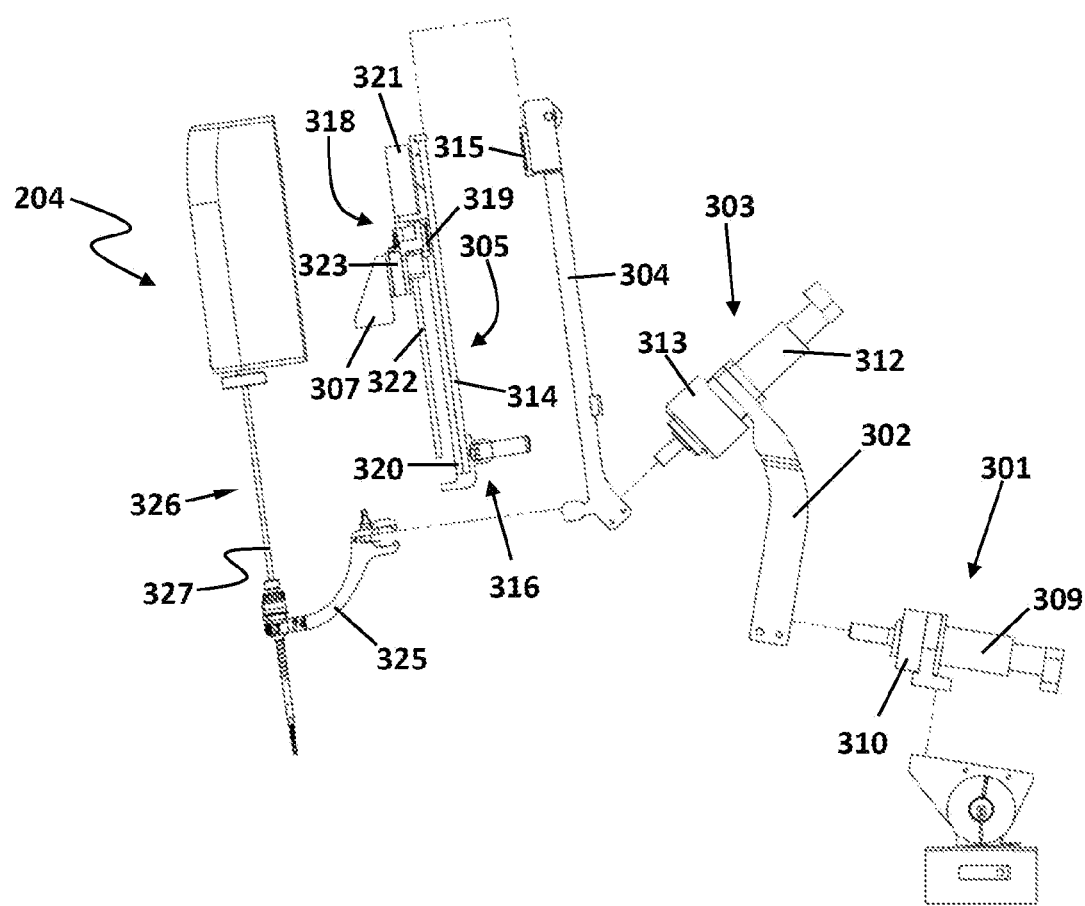
FIG. 3C illustrates a left view of one implementation of an example slave robotic arm for a robotic tele-surgery system, consistent with one or more exemplary embodiments of the present disclosure.

FIG. 3A shows an assembled view of one example of a slave robotic arm 203. FIG. 3B shows an exploded view of the slave robotic arm. FIG. 3C shows an exploded left view of the slave robotic arm.

Referring to FIG. 3A, the slave robotic arm 203 may include a first actuating mechanism 301, a first arm segment 302, a second actuating mechanism 303, a second arm segment 304, a passive actuating mechanism 305, an active actuating mechanism 306, and a tool attachment interface 307.

Referring to FIGS. 3A-3C, the first actuating mechanism 301 may be configured for driving a roll rotation of the first arm segment 302 about a first rotational axis 308. The first actuating mechanism 301 may include a first motor 309 coupled with a base end of the first arm segment 302 via a first gear box 310. The first motor 309 and the first gear box 310 may be configured to drive the roll rotation of the first arm segment 302 about the first rotational axis 308. The first gear box 310 may be, for example, a harmonic drive gear box.

Referring to FIGS. 3A-3C, the second actuating mechanism 303 may be mounted on a distal end of the first arm segment 302 and may be configured for driving a rotational movement of the second arm segment 304 about a second rotational axis 311. The second actuating mechanism 303 may include a second motor 312 and a second gearbox 313. The second motor 312 may be coupled with a proximal end of the second arm segment 304 via the second gear box 313. The second motor 312 and the second gear box 313 may be configured to drive a rotational movement of the second arm segment 304 about the second rotational axis 311.

Referring to FIGS. 3A-3C, the passive actuating mechanism 305 may include a passive track 314, a passive wagon 315, and a passive locking mechanism 316. The passive wagon 315 may be attached to the distal end of the second arm segment 304 and it may be configured to facilitate a sliding movement of the passive track 314 along a translational axis 317. The passive actuating mechanism 305 may be actuated by hand and it may be utilized to facilitate changing the instrument 326 by raising the tool adapting mechanism 204. The height of the instrument 326 may also be adjusted utilizing the passive actuating mechanism 305.

Referring to FIGS. 3A-3C, the active actuating mechanism 306 may include a linear actuating mechanism 318, a moving wagon 319 and an active track 320 that is attached to the passive track 314 of the passive actuating mechanism 305. The linear actuating mechanism 318 may include a motor 321 and a ball-screw mechanism 322. The linear actuating mechanism 318 may be mounted on the moving wagon 319 and the moving wagon 319 may be slidably mounted on the active track 320. The linear actuating mechanism 318 is configured to facilitate the linear translational movement of the moving wagon 319 on the active track 320 along the translational axis 317. A force sensor 323 may be mounted on the active actuating mechanism 306 from one side and to the tool attachment interface 307 from the other side. The force sensor 323 may be configured for sensing force/torque exerted on a laparoscopic instrument 326 that is attached via the tool attachment interface 307 to the active actuating mechanism 306 on the distal end of the slave robotic arm 203.

Referring to FIG. 3B, the tool adapting mechanism 204 may be attached to the distal end of the slave robotic arm 203 via the tool attachment interface 307. The tool adapting mechanism 204 may activate DOFs of a laparoscopic surgical instrument 326 to interact with a tissue under surgery. The second arm segment 304 may be attached to a sleeve holder 325 that may be configured for holding a sleeve 327 of the laparoscopic surgical instrument 326 for more stability.

Surgeon-Side Unit

Figure 4A:
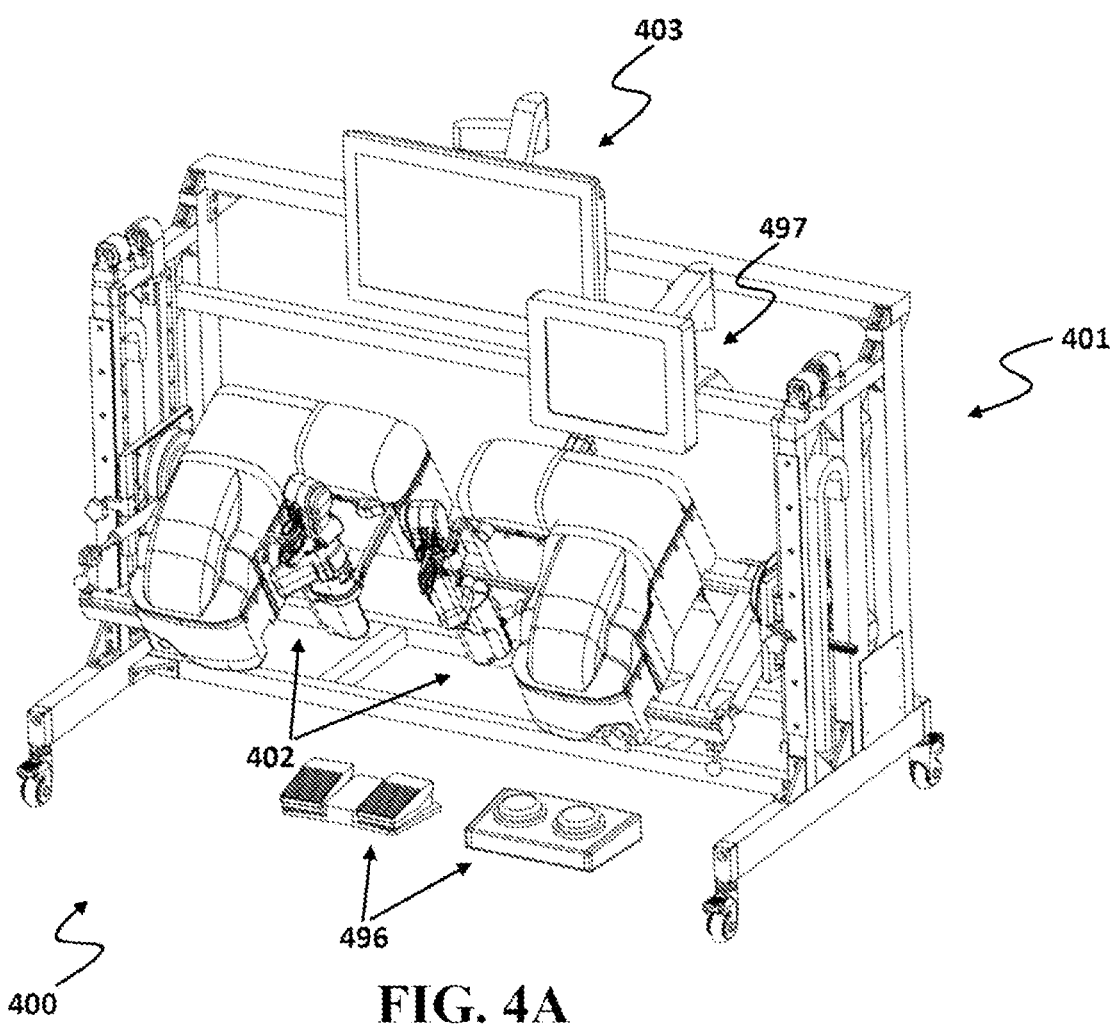
FIG. 4A illustrates one implementation of an example surgeon-side unit for one robotic tele-surgery system, consistent with one or more exemplary embodiments of the present disclosure.

FIG. 4A shows a perspective view of one example surgeon-side unit 400. Referring to FIG. 4A, the surgeon-side unit 400 may include an ergonomic adjustment mechanism 401, two master robotic arms 402, a display system 403, and a user interface unit 497. The ergonomic adjustment mechanism 401 may be configured for adjusting the position and orientation of the master robotic arms 402 using three DOFs.

Figure 4B:
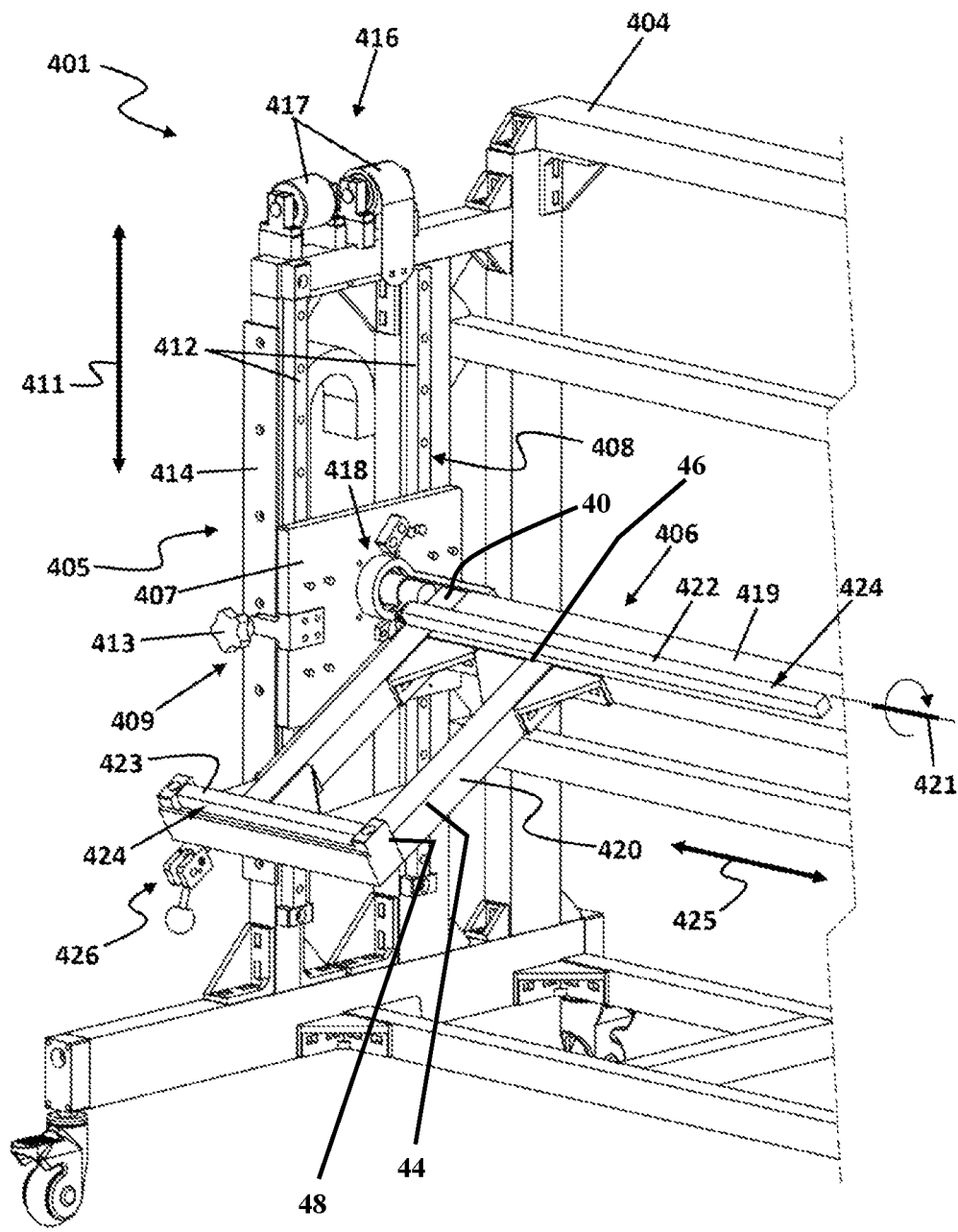
FIG. 4B illustrates a partial view of one implementation of an example ergonomic adjustment mechanism for the surgeon-side unit of one robotic tele-surgery system, consistent with one or more exemplary embodiments of the present disclosure.
Figure 4C:
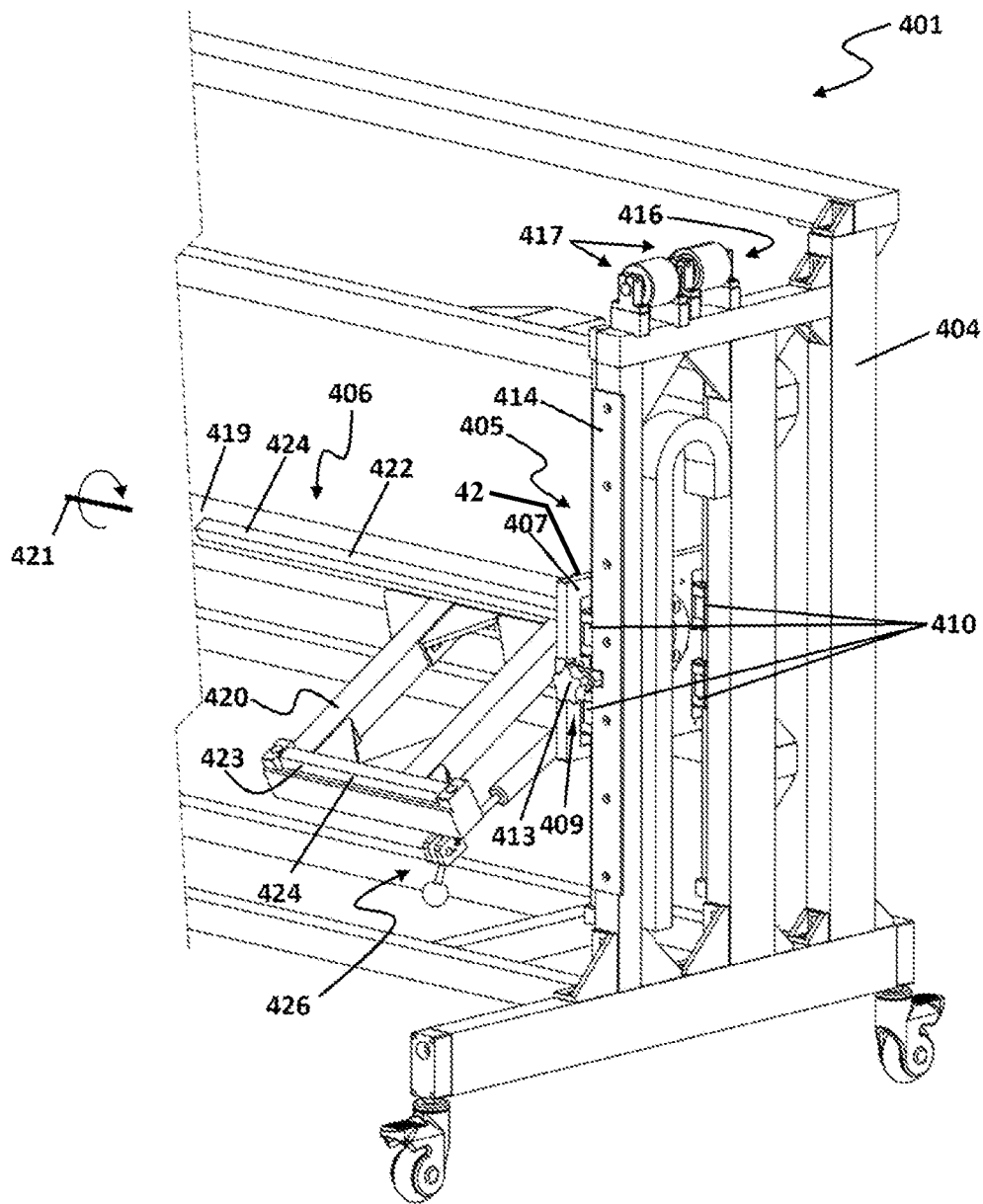
FIG. 4C illustrates a partial view of one implementation of an example ergonomic adjustment mechanism for the surgeon-side unit of one robotic tele-surgery system, consistent with one or more exemplary embodiments of the present disclosure.

Referring to FIGS. 4B and 4C, the ergonomic adjustment mechanism 401 may include a main frame 404, a vertical adjustment mechanism 405, and a horizontal adjustment mechanism 406. The vertical adjustment mechanism 405 may be mounted on the main frame 404 and it may include a sliding assembly 407, a vertical track assembly 408 and a locking mechanism 409 on either side of the ergonomic adjustment mechanism 401. The sliding assembly 407 may include a plurality of sliding wagons 410 that may be slidably mounted on the vertical track assembly 408 and may be configured to facilitate the vertical translational movement of the sliding assembly 407 along a substantially vertical axis 411. The vertical track assembly 408 may include two parallel rails 412 configured to allow for a translational movement of the wagons 410 along the axis 411. The locking mechanism 409 may include a locking screw 413 and a vertically extended locking plate 414 having a plurality of stacked locking holes that allow for locking the sliding assembly 407 at different heights based on the preference of a user (i.e., a surgeon). The vertical track assembly 408 may further include a counter weight mechanism 416 that may include a plurality of constant-force spring mechanisms 417. The counter weight mechanism 416 may be configured to facilitate vertical movements of the sliding assembly 407. The sliding assembly 407 may further include a coupling member 418 that may be for example a bearing unit that may be configured to allow for mounting the horizontal adjustment mechanism 406 between the sliding assemblies 407 on either side of the ergonomic adjustment mechanism 401.

The horizontal adjustment mechanism 406 may be rotatably mounted on the vertical adjustment mechanism via the coupling member 418 and it may include a main shaft 419, and two mounting platforms 420. The main shaft 419 may be coupled via the coupling members 418 with the sliding assemblies 407 of the vertical adjustment mechanism 405. The coupling members 418 may be configured to allow for a rotational movement of the shaft 419 about a rotational axis 421. A horizontal rail 422 may be attached to the main shaft 419 and a smaller rail 423 may be attached to the mounting platform 420 to form a horizontal track assembly 424 that may be configured for facilitating a horizontal movement of the master robotic arms 402 along a horizontal axis 425. Weight balance mechanisms 426 may be used to stabilize the mounting platforms 420 in position. The weight balance mechanisms 426 may include gas spring mechanisms. The three DOFs (i.e., two linear DOFs along axes 411, 425 and one linear DOF about axis 421) of the ergonomic adjustment mechanism 401 may be locked in position during surgery.

Figure 4D:
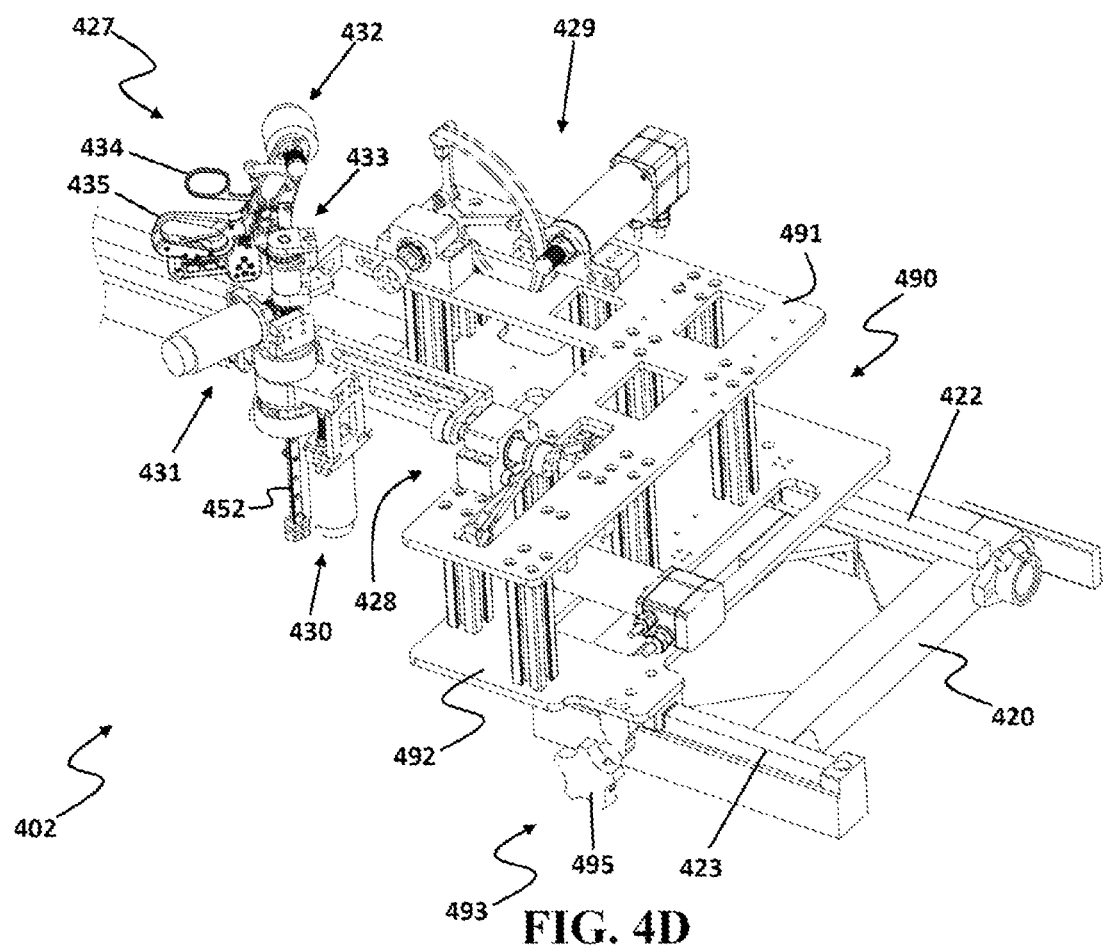
FIG. 4D illustrates one implementation of an example master robotic arm for one robotic tele-surgery system, consistent with one or more exemplary embodiments of the present disclosure.

Referring to FIG. 4D, the master robotic arm 402 may include a master handle 427, a pitch sensing/actuating mechanism 428, a yaw sensing/actuating mechanism 429, a roll sensing/actuating mechanism 430, an insert sensing/actuating mechanism 431, a grasp sensing/actuating mechanism 432, and a finger-roll sensing/actuating mechanism 433.

Figure 4E:
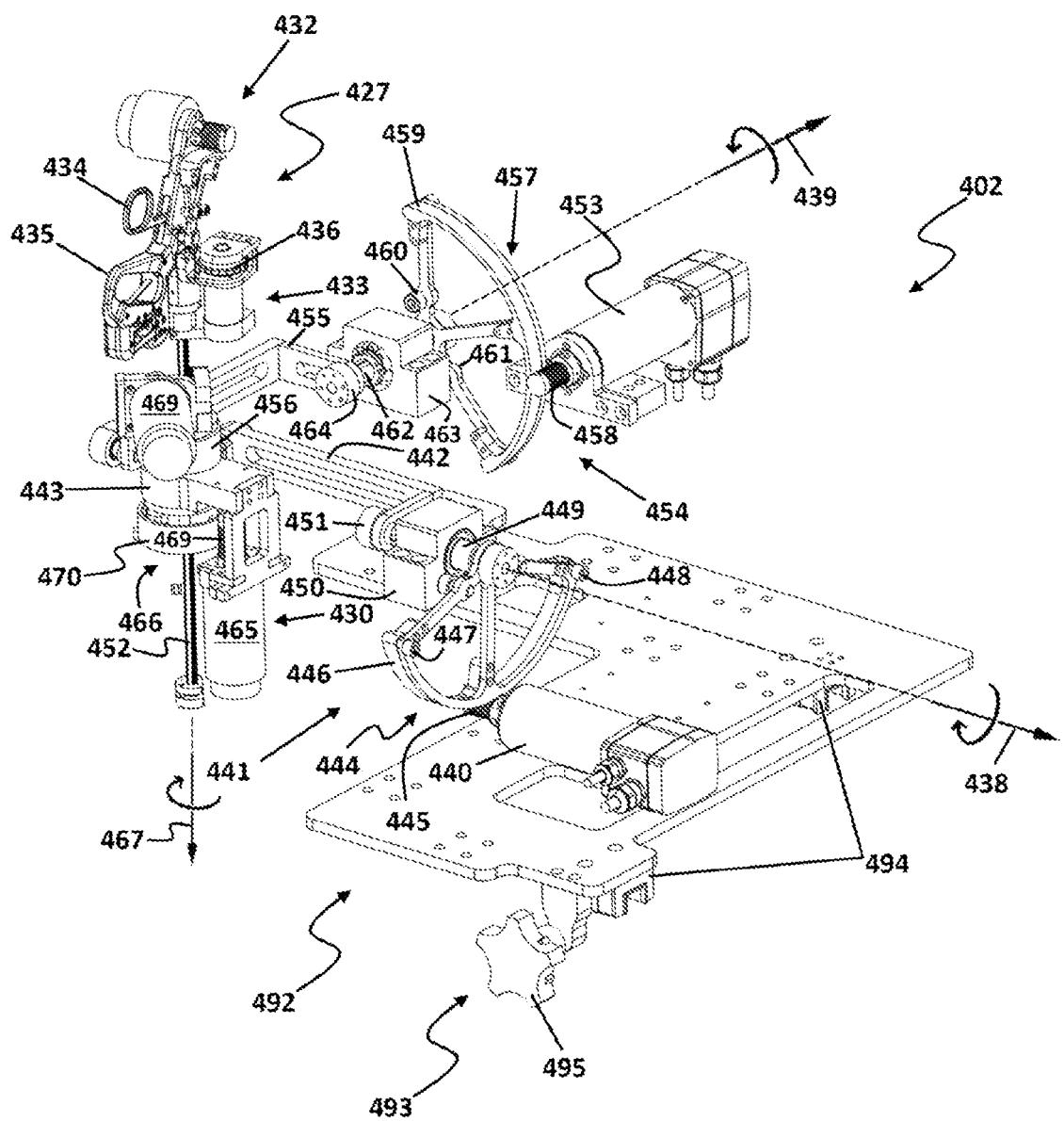
FIG. 4E illustrates one implementation of an example master robotic arm without the mounting platform for one robotic tele-surgery system, consistent with one or more exemplary embodiments of the present disclosure.
Figure 4F:
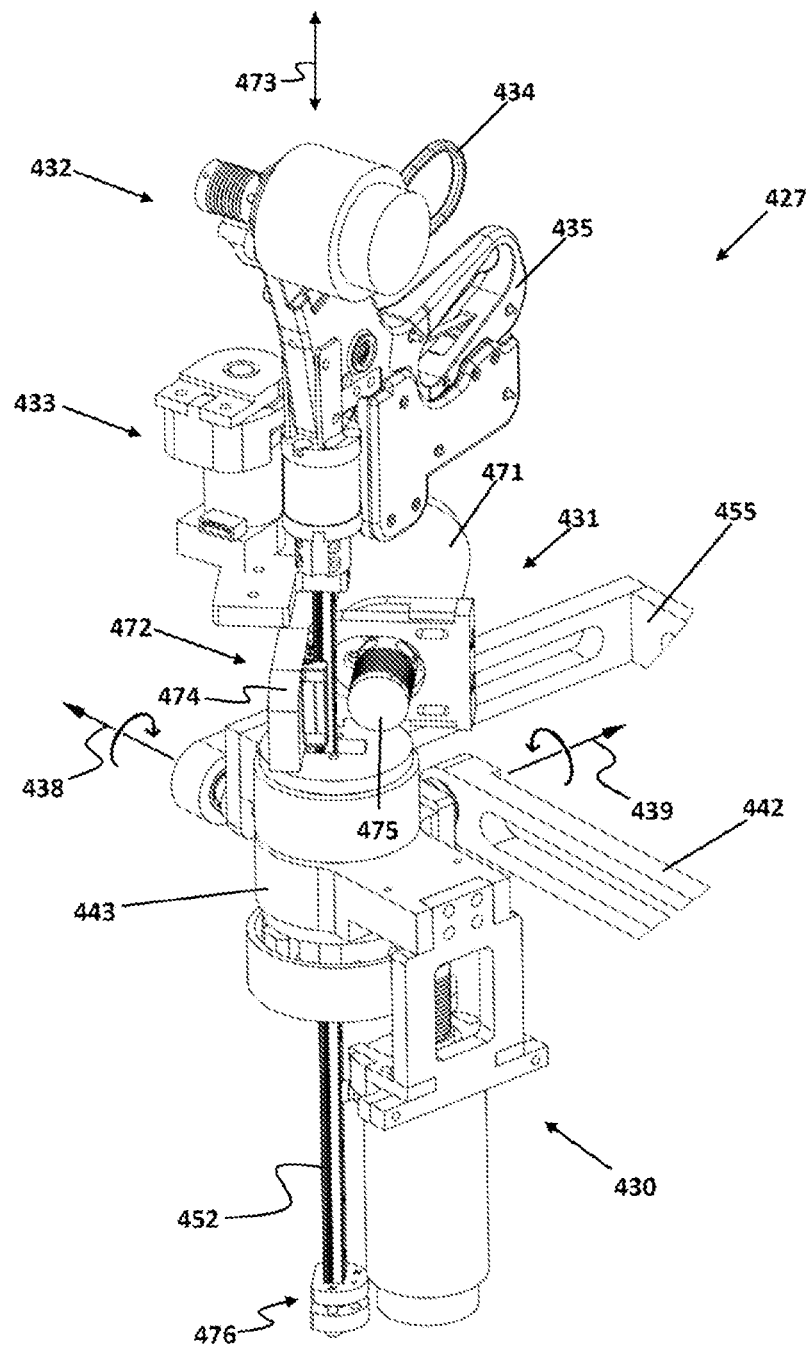
FIG. 4F illustrates one implementation of an example master handle of a master robotic arm for one robotic tele-surgery system, consistent with one or more exemplary embodiments of the present disclosure.
Figure 4G:
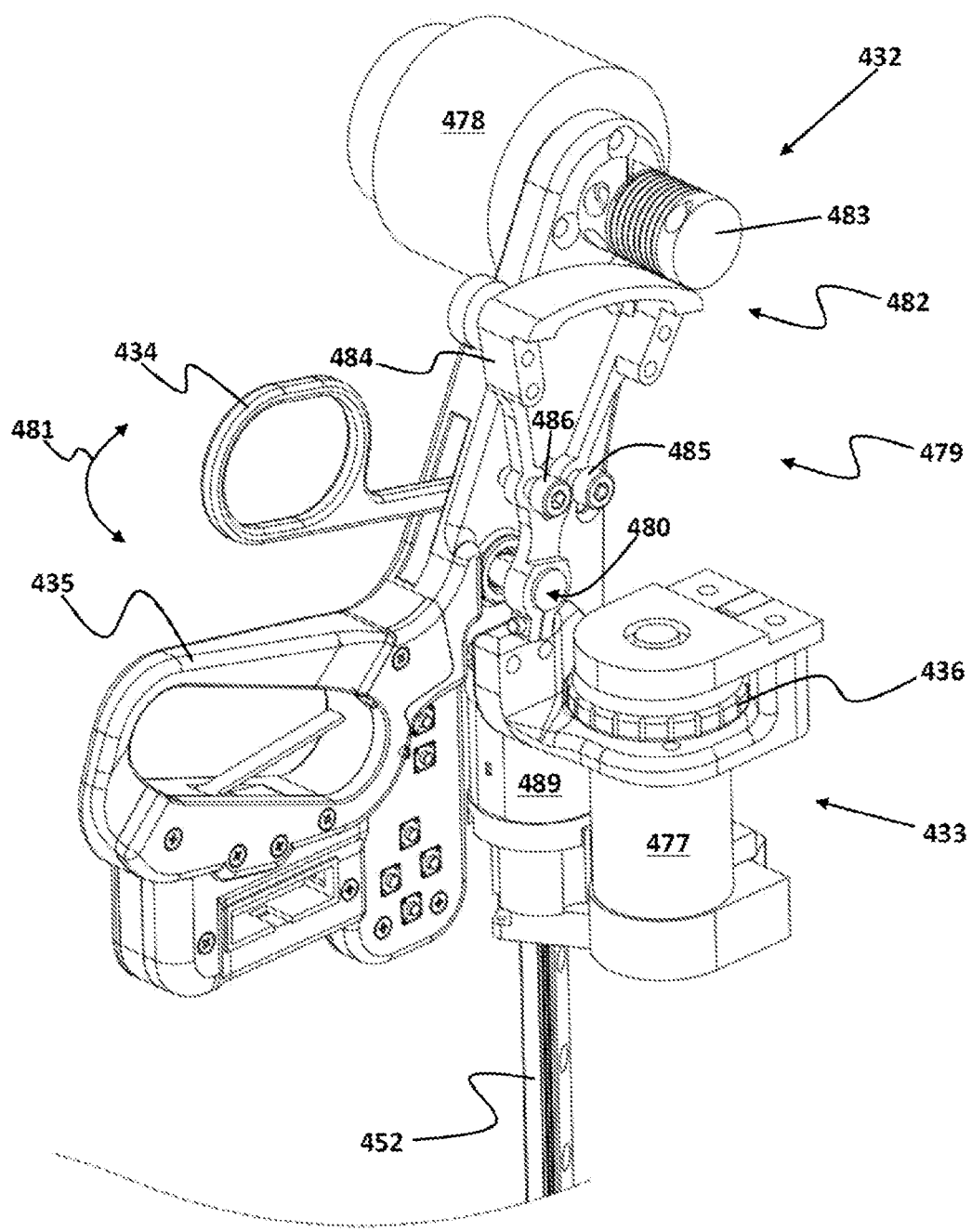
FIG. 4G illustrates a top portion of one implementation of an example master handle of a master robotic arm for one robotic tele-surgery system, consistent with one or more exemplary embodiments of the present disclosure.

Referring to FIG. 4G, the master handle 427 may be structured similar to a manual surgical instrument. The master handle 427 may be manipulated by hand of a user (i.e., surgeon) and it may include a scissor-type configuration having a movable handle 434, a stationary handle 435, and a roll-knob 436. Referring to FIG. 4F, the user may manipulate the tool handle 427 to make pitch and yaw rotational movements about a pitch axis 438 and a yaw axis 439. Each master handle 427 on each master robotic arm 402 may be associated with one slave robotic arm 203 and the tool adapting mechanism 204 attached thereto.

Referring to FIGS. 4D and 4E, the pitch sensing/actuating mechanism 428 may include: a pitch rotary actuator 440, for example, an electric motor; a pitch transmission mechanism 441; a pitch link arm 442 and a pitch gimbal 443. The pitch sensing/actuating mechanism 428 may be configured for both capturing the pitch position of the tool handle 427 and creating pitch force feedback to the tool handle for providing a haptic sensation. As used herein, "capturing the pitch position" may mean sensing the amount of rotational movement of the tool handle 427 about the pitch axis 438.

Referring to FIG. 4E, the pitch transmission mechanism 441 may include: a pitch cable transmission mechanism 444 having a spool 445 coupled with the pitch rotary actuator 440; a pitch rotary output member 446 that may be coupled with the spool 445 using a cable secured form one side to a first pitch cable connector 447 and form the other side to a second pitch cable connector 448, such that the torque from the pitch rotary actuator 440 may be transmitted via the cable to the pitch rotary output member 446. The pitch rotary output member 446 may be coupled with a pitch shaft 449 and the pitch shaft 449 may be held in place using a pitch bearing unit 450 and it may be coupled with the pitch link arm 442 via a pitch coupling member 451. The pitch coupling member 451 may define a joint which allows the pitch link arm 442 to articulate. The pitch link arm 442 may articulate bi-directionally, in response to corresponding rotation of the pitch shaft 449 about the pitch axis 438. The pitch link arm 442 may be attached to the pitch gimbal 443. The pitch gimbal 443 may be connected to a central rail 452 attached to the tool handle 427.

Referring to FIG. 4E, the yaw sensing/actuating mechanism 429 may include: a yaw rotary actuator 453, for example, an electric motor; a yaw transmission mechanism 453; a yaw link arm 455 and a yaw gimbal 456. The yaw sensing/actuating mechanism 429 may be configured for both capturing the yaw position of the tool handle 427 and creating yaw force feedback to the tool handle for providing a haptic sensation. As used herein, "capturing the yaw position" may mean sensing the amount of rotational movement of the tool handle 427 about the yaw axis 439.

The yaw transmission mechanism 454 may include: a yaw cable transmission mechanism 457 having a spool 458 coupled with the yaw rotary actuator 453; a yaw rotary output member 459 that may be coupled with the spool 458 using a cable secured form one side to a first yaw cable connector 460 and from the other side to a second yaw cable connector 461, such that the torque from the yaw rotary actuator 453 may be transmitted via the cable to the yaw rotary output member 459. The yaw rotary output member 459 may be coupled with a yaw shaft 462 and the yaw shaft 462 may be held in place using a yaw bearing unit 463 and it may be coupled with the yaw link arm 455 via a yaw coupling member 464. The yaw coupling member 464 may define a joint which allows the yaw link arm 455 to articulate. The yaw link arm 455 may articulate bi-directionally, in response to corresponding rotation of the yaw shaft 462 about the yaw axis 439. The yaw link arm 455 may be attached to the yaw gimbal 456. The yaw gimbal 456 may be connected to the central rail 452.

In an implementation, the pitch gimbal 443 and the yaw gimbal 456 may be mounted on one another with orthogonal pivot axes (i.e., pitch axis 438 and yaw axis 439) on the master handle 427. Any pitch-rotational movement made by the user may be picked up by the pitch gimbal 443 and it may be transmitted to the pitch rotary actuator 440 via the pitch link arm 442 and the pitch transmission mechanism 441. The pitch-rotational movement of the handle 427 may then be encoded and transmitted by the controller that is connected to the driver of the pitch rotary actuator 440 to the slave robotic arm for the pitch movement to be recreated by the slave robotic arm in the patient-side unit. Any yaw-rotational movement made by the user may be picked up by the yaw gimbal 456 and it may be transmitted to the yaw rotary actuator 453 via the yaw link arm 455 and the yaw transmission mechanism 454. The yaw-rotational movement of the handle 427 may then be encoded and transmitted by the controller that is connected to the driver of the yaw rotary actuator 453 to the slave robotic arm for the yaw movement to be recreated by the slave robotic arm in the patient-side unit.

Referring to FIG. 4E, the roll sensing/actuating mechanism 430 may include: a roll rotary actuator 465, for example, an electric motor; and a roll transmission mechanism 466. The roll sensing/actuating mechanism 430 may be configured for both capturing the roll position of the tool handle 427 and creating a roll force feedback to the tool handle 427 for providing a haptic sensation. As used herein, "capturing the roll position" may mean sensing the amount of rotational movement of the tool handle 427 about a roll axis 467.

The roll transmission mechanism 466 may include: a roll cable transmission mechanism having a spool 469 coupled with the roll rotary actuator 465; and a yaw rotary output member 470 that may be coupled with the spool 469 using a cable. The roll rotary output member 470 may be connected to the central rail 452. The roll transmission mechanism 466 may be configured to transmit the roll-rotation of the roll rotary actuator 465 to the central rail 452 and it may be configured to pick up any roll-rotation movements made by the surgeon on the master handle 427. The roll-rotational movement of the handle 427 may then be encoded and transmitted by the controller that is connected to the driver of the roll rotary actuator 464 to the slave robotic arm for the yaw movement to be recreated by the slave robotic arm in the patient-side unit.

Referring to FIG. 4F, the insert sensing/actuating mechanism 431 may include: an insert rotary actuator 471, for example, an electric motor; and an insert transmission mechanism 472. The insert sensing/actuating mechanism 431 may be configured for both capturing the insert position (i.e., position of the surgical tool along its longitudinal axis) of the tool handle 427 and creating an insert force feedback to the tool handle 427 for providing a haptic sensation. As used herein, "capturing the insert position" may mean sensing the amount of translational movement of the tool handle 427 along a tool handle longitudinal axis 473.

The insert transmission mechanism 472 may include an insert wagon 474 that may be mounted on the yaw gimbal 456. The insert wagon 474 may be slidably mounted on the central rail 452 and it may be configured for facilitating a translational sliding movement of the central rail 452 along the longitudinal axis 473 of the master handle 427. A spool 475 may be coupled with the insert rotary actuator 471 and it may be secured on a cable connecting member 476 at a distal end of the central rail 452. The cable moves the central rail 452 in a translational movement along the longitudinal axis 473 of the tool handle 427 upon actuation. The position of the tool handle 427 along the longitudinal axis (i.e., insert position) may be picked up by the central rail 452 and it may be transmitted through the cable to the insert rotary actuator 471. The insert position of the handle 427 may then be encoded and transmitted by the controller that is connected to the driver of the insert rotary actuator 471 to the slave robotic arm for the insert movement to be recreated by the slave robotic arm in the patient-side unit.

Referring to FIG. 4G, the finger-roll sensing/actuating mechanism 433 may include: a finger-roll rotary actuator 477, for example, an electric motor coupled with the roll knob of the tool handle. The finger-roll sensing/actuating mechanism 433 may be configured for both capturing the finger-roll position of the roll-knob 436 on the tool handle 427 and creating a force feedback to the roll-knob 436 of the tool handle 427 for providing a haptic sensation. As used herein, "capturing the finger-roll position" may mean sensing the amount of rotational movement of the roll-knob 436 on the tool handle 427. The finger-roll transmission mechanism 433 may be configured to transmit the roll-rotation of the finger-roll rotary actuator 477 to the roll-knob 436 and it may be configured to pick up any roll-rotation movements made by the surgeon on the roll-knob 436. The roll-rotational movement of the roll-knob 436 may then be encoded and transmitted by the controller that is connected to the driver of the finger-roll rotary actuator 464 to the slave robotic arm for the roll-knob movement to be recreated by the slave robotic arm in the patient-side unit. Referring to FIGS. 4G and 2B, the roll-rotational movement of the roll-knob 436 may drive a local roll-rotation of the end-effector 248 of the surgical instrument 247 about a local roll axis parallel to a longitudinal axis of the end-effector.

Referring to FIG. 4G, the grasp sensing/actuating mechanism 432 may include: a grasp rotary actuator 478, for example, an electric motor; and a grasp transmission mechanism 479. The grasp sensing/actuating mechanism 432 may be configured for both capturing the grasp position of the movable handle 434 and creating a grasp force feedback to the movable handle 434 for providing a haptic sensation. As used herein, "capturing the grasp position" may mean sensing the amount of rotational movement of the movable handle 434 about a pivot point 480 in the direction shown by an arrow 481.

The grasp transmission mechanism 479 may include: a grasp cable transmission mechanism 482 having a spool 483 coupled with the grasp rotary actuator 478; and a grasp output member 484 that may be coupled with the spool 483 using a cable secured on one side to a first grasp cable connecting member 485 and on the other side to a second grasp cable connecting member 486. The grasp output member 484 may be connected to the movable handle 434. The grasp transmission mechanism 479 may be configured to transmit the rotation of the grasp rotary actuator 478 to the movable handle 434 and it may be configured to pick up any grasp movements made by the surgeon on the movable handle 434. The grasp movement of the movable handle 434 may then be encoded and transmitted by the controller that is connected to the driver of the grasp rotary actuator 478 to the slave robotic arm for the grasp movement to be recreated by the slave robotic arm in the patient-side unit.

Referring to FIGS. 4E and 4G, the master handle 427 may further comprise a force sensor 489 that may be configured to measure force/torque exerted on the master handle 427. The force sensor 489 may be utilized to make sure the same amount of force/torque feedback is being recreated by the actuating mechanisms 428-433 in the surgeon side-unit 400 as is exerted on the surgical tool in the patient-side unit.

Referring to FIG. 4D, the master robotic arm 402 may further include a mounting assembly 490 that may include a support structure 491, a sliding mechanism 492, and a locking mechanism 493. The support structure 491 may be configured to provide a platform for mounting of various components of the master robotic arm 402. The sliding mechanism 492 may include a plurality of sliding wagons 494 that may be slidably mounted on the horizontal track assembly 424 to facilitate a translational movement of the master robotic arm 402 along the horizontal axis 425. The locking mechanism 493 may include a locking screw 495 that may be configured to allow for locking the sliding wagons 494 in desired positions on the horizontal sliding track 424.

Referring to FIG. 4A, the surgeon-side unit 400 may further include input means 496 for controlling a camera inserted in the patient's body and for applying cauterizing current to the surgical tool attached on the distal end of the slave robotic arm.

Figure 5:
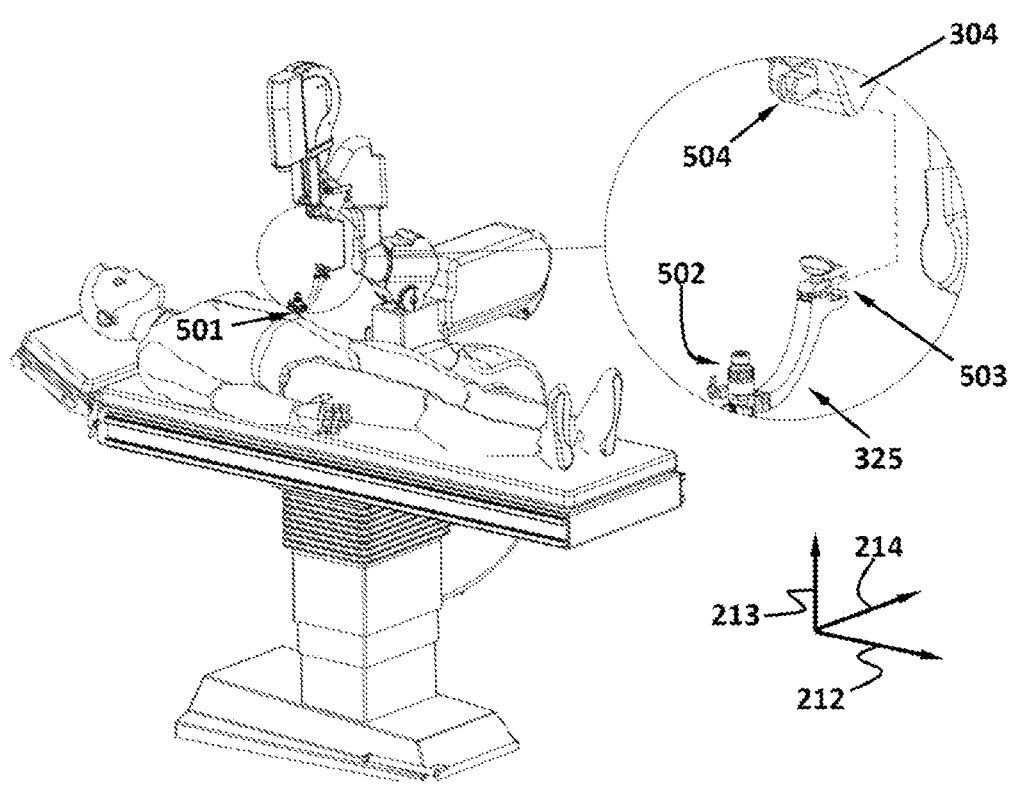
FIG. 5 illustrates an exemplary scenario for aligning a fixed point (i.e., remote center of motion) of the robotic arms with the incision location on patient's body utilizing the passive mounting mechanism, consistent with one or more exemplary embodiments of the present disclosure.

FIG. 5 illustrates an exemplary scenario for aligning a fixed point (i.e., remote center of motion) of the robotic arms with the incision location on patient's body utilizing the passive mounting mechanism, consistent with exemplary embodiments of the present disclosure. First, based on the type of surgery and the target organ, the incision points on the patient's body are determined by the surgeon. Sometimes an optimizing program (not in the scope of the present disclosure) may be used in order to optimize the incision locations. The optimizing program, optimizes the incision locations for better maneuverability of the robotic arms. The incision is made in the determined incision location. The surgical instrument is placed inside the incision.

Before the surgery, the surgeon determines the pan and tilt angles of the slave robotic arm 203 based on the type of surgery and the target organ. The pan and tilt DOFs can be adjusted utilizing the pan/tilt mounting mechanism 211. Pan and tilt are passive DOFs and once they are adjusted by the surgeon before surgery, they will be locked during the surgery.

Referring to FIG. 5, once the incision is made in the pre-determined incision location 501, the surgical instrument 326 that is secured inside a holding member 502 on the distal end of the sleeve holder 325, will be inserted inside the incision. Then, the surgeon must adjust the position of the slave robotic arm 203 such that the proximal end of the sleeve holder 325 can be clamped on an attachment member 504 on the second arm segment 304. Utilizing the three DOFs 212, 213, and 214 of the passive mounting mechanism 110 the surgeon is able to place the attachment member 504 inside a clamping member 503 on the proximal end of the sleeve holder 325 and clamp the sleeve holder 325 to the slave robotic arm 203.

Ergonomic Adjustment Mechanism

According to one or more exemplary embodiments, the present disclosure is directed to exemplary embodiments of an ergonomic adjustment mechanism, such as ergonomic adjustment mechanism 401 for a surgeon-side unit of a robotic tele-surgery system, such as surgeon-side unit 400. An exemplary ergonomic adjustment mechanism may provide various DOFs that may allow a surgeon to perform laparoscopic surgery at various ergonomic positions. Exemplary ergonomic positions may include a standing position, a sitting position, and a semi-sitting position.

Referring to FIGS. 4B and 4C, in an exemplary embodiment, ergonomic adjustment mechanism 401 may include vertical adjustment mechanism 405 that may be configured to move a master robotic arm, such as master robotic arms 402 along vertical axis 411. In an exemplary embodiment, vertical adjustment mechanism 405 may include a horizontal beam, such as main shaft 419 that may be extended along horizontal axis 425 between a first end 40 and a second end 42. In an exemplary embodiment, horizontal axis 425 may be perpendicular to vertical axis 411. In an exemplary embodiment, vertical adjustment mechanism 405 may further include a linear actuator that may be coupled to the horizontal beam. An exemplary linear actuator may be configured to actuate a translational movement of the horizontal beam along vertical axis 411. In an exemplary embodiment, an exemplary linear actuator may include a first vertical track such as vertical track assembly 408 that may be slidably coupled with first end 40 of the horizontal beam. The first vertical track may be configured to guide a linear translational movement of first end 40 along vertical axis 411. In an exemplary embodiment, an exemplary linear actuator may further include a second vertical track (not labeled) that may be slidably coupled with second end 42 of the horizontal beam. An exemplary second vertical track may be configured to guide a linear translational movement of second end 42 along vertical axis 411.

In an exemplary embodiment, the first vertical track may be similar to vertical track assembly 408 and may include a couple of parallel sliding rails such as parallel rails 412 that may extend along vertical axis 411, and sliding wagon 410 that may be slidably mounted on the couple of parallel sliding rails. Sliding wagon 410 may be moveable along vertical axis 411. In an exemplary embodiment, the first sliding wagon may include a first bearing unit such as coupling member 418 that may be rotatably coupled with first end 40 of the horizontal beam. In an exemplary embodiment, the first bearing unit may allow for a rotational movement of the horizontal beam about rotational axis 421. In an exemplary embodiment, the second vertical track may be structurally similar to the first vertical track.

In an exemplary embodiment, sliding wagon 410 may further include a first lock (its parts are described below, so please label this as well) that may be configured to lock sliding wagon 410 in position at a desirable height along vertical axis 411. In an exemplary embodiment, the first lock XXX may include locking screw 413 and vertically extended locking plate 414. In an exemplary embodiment, vertically extended locking plate 414 may include a plurality of stacked locking holes (label), where each respective hole of stackee locking holes may be at a predetermined height (from what??_along vertical axis 411. Each respective hole of . . . may be configured to receive locking screw 413 therein. As used herein, receiving receive locking screw 413 inside a respective locking hole may refer to screwing locking screw 413 into a locking hole.

In an exemplary embodiment, ergonomic adjustment mechanism 401 may further include horizontal adjustment mechanism 406 that may be configured to move a master robotic arm, such as master robotic arms 402 along horizontal axis 425. In an exemplary embodiment, horizontal adjustment mechanism 406 may include a horizontal sliding rail such as horizontal track assembly 424. In an exemplary embodiment, horizontal track assembly 424 may be mounted on main shaft 419. In an exemplary embodiment, horizontal track assembly 424 may be parallel with main shaft 419. In an exemplary embodiment, master robotic arms 402 may be slidably mounted on horizontal track assembly 424. In an exemplary embodiment, master robotic arms 402 may be moveable along horizontal axis 425 on the horizontal sliding rail. In an exemplary embodiment, horizontal adjustment mechanism 406 may further include a link 44 that may radially extend outward from main shaft 419 between a proximal end 46 and a distal end 48. Proximal end 46 of link 44 may be attached to main shaft 419. The horizontal sliding rail may be mounted on distal end 48 of link 44.

Figure 6A:
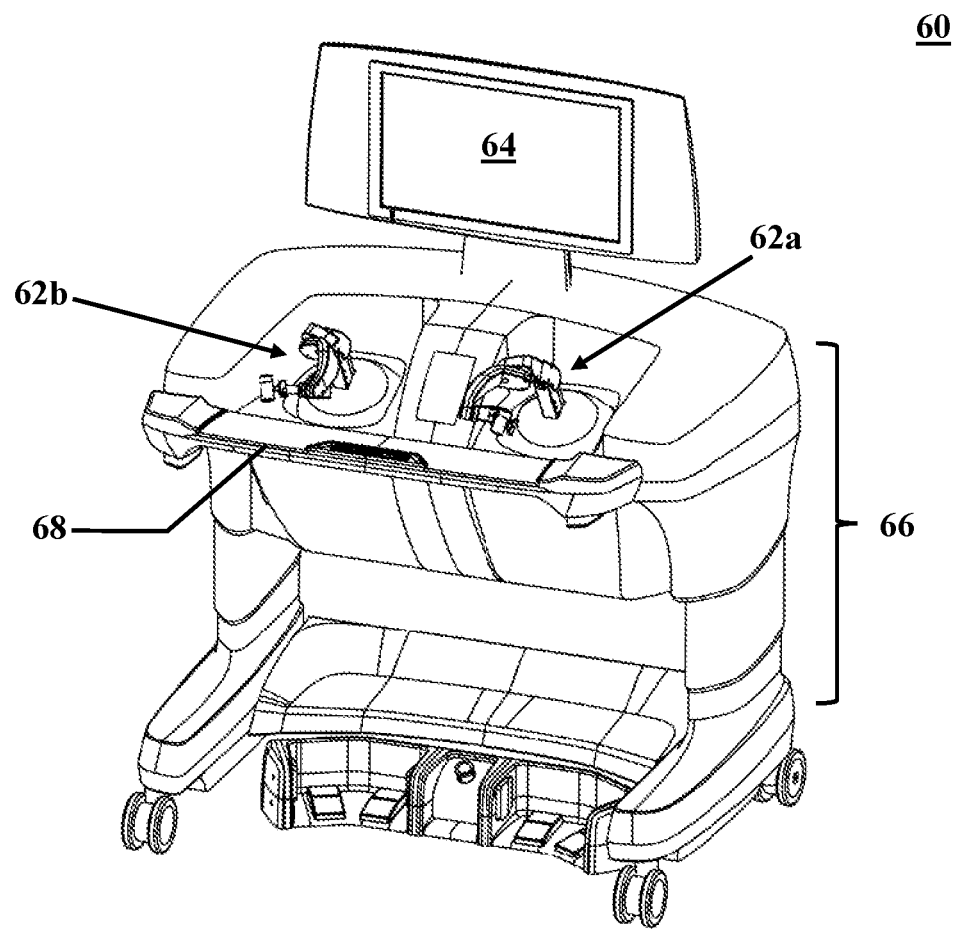
FIG. 6A illustrates an ergonomic master console, consistent with one or more exemplary embodiments of the present disclosure.
Figure 6B:
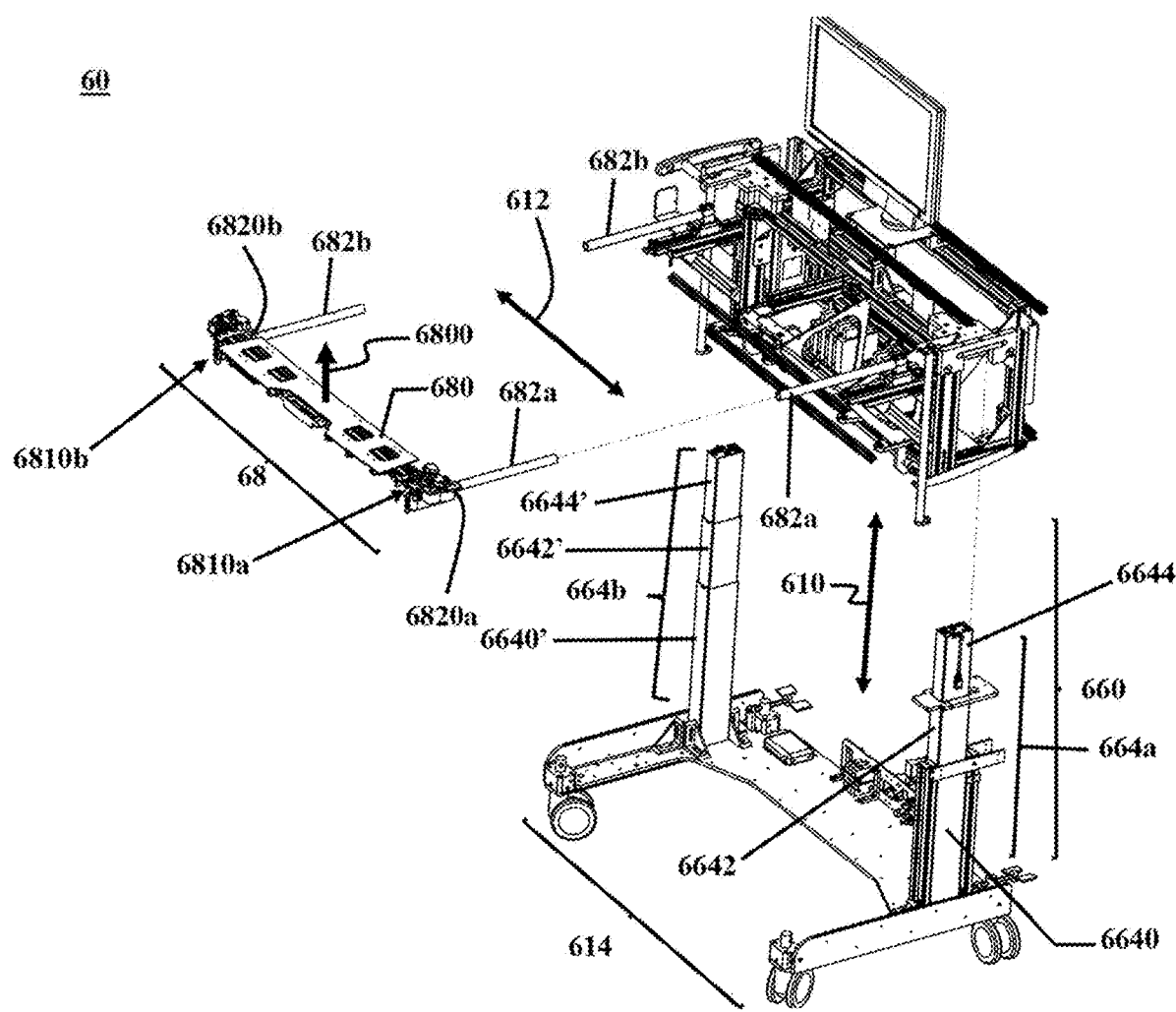
FIG. 6B illustrates an exploded perspective view of an ergonomic master console, consistent with one or more exemplary embodiments of the present disclosure.
Figure 6C:
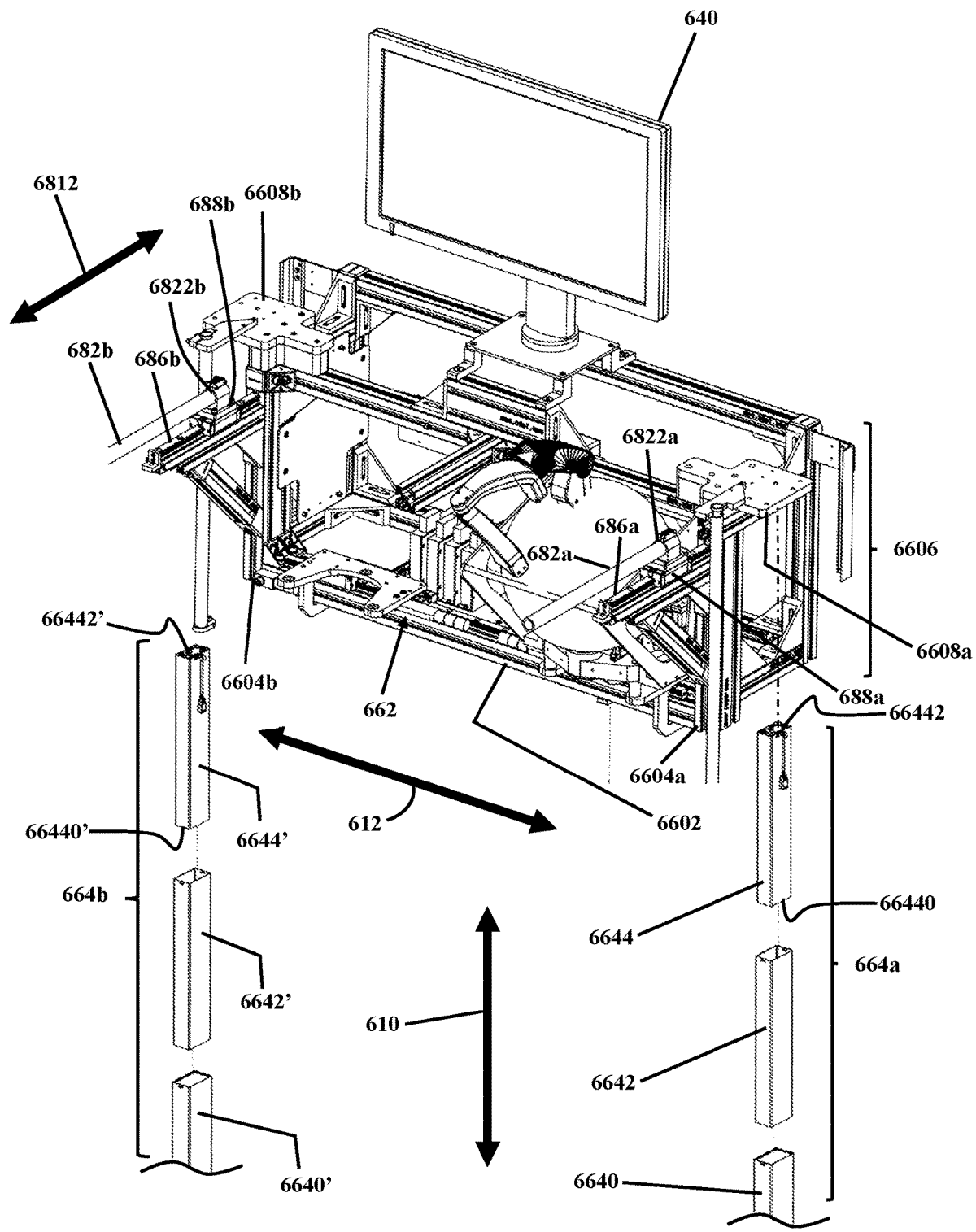
FIG. 6C illustrates an exploded perspective view of an upper portion of an ergonomic master console, consistent with one or more exemplary embodiments of the present disclosure.

FIG. 6A illustrates an ergonomic master console 60, consistent with one or more exemplary embodiments of the present disclosure. FIG. 6B illustrates an exploded perspective view of ergonomic master console 60, consistent with one or more exemplary embodiments of the present disclosure. FIG. 6B illustrates an exemplary embodiment of ergonomic master console 60 without covers to allow for the internal parts of ergonomic master console 60 to be visible. FIG. 6C illustrates an exploded perspective view of an upper portion of ergonomic master console 60, consistent with one or more exemplary embodiments of the present disclosure.

In an exemplary embodiment, ergonomic master console 60 may be functionally similar to surgeon-side unit 400. In an exemplary embodiment, ergonomic master console 60 may include master robotic arms 62*a-b* that may be functionally similar to master robotic arms 402 and a user-interface unit 64 that may be functionally similar to user interface unit 497. In an exemplary embodiment, master robotic arms 62*a-b* and user-interface unit 64 may be coupled to and mounted on an ergonomic adjustment mechanism 66. In an exemplary embodiment, ergonomic adjustment mechanism 66 may adjust the position and orientation of master robotic arms 62*a-b* and user-interface unit 64. In an exemplary embodiment, ergonomic master console 60 may further include a hand-rest assembly 68 that may allow a surgeon to rest their arms on hand-rest assembly 68 while using master robotic arms 62*a-b*, thus creating a more comfortable situation for a surgeon.

In an exemplary embodiment, ergonomic adjustment mechanism 66 may include a vertical adjustment mechanism 660 that may be configured to move master robotic arms 62*a-b* along a vertical axis 610. In an exemplary embodiment, vertical adjustment mechanism 660 may include a horizontal beam 6602 extended along a horizontal axis 612 between a first end 6604*a* and a second end 6604*b*. In an exemplary embodiment, a linear actuator (not illustrated???) may be coupled to horizontal beam 6602, where the linear actuator may be configured to actuate a translational movement of horizontal beam 6602 along vertical axis 610.

In an exemplary embodiment, a linear actuator may be coupled to horizontal beam 6602 to actuate a translational movement of horizontal beam 6602 along vertical axis 610. An exemplary linear actuator may include a first telescopic jack 664*a* that may be coupled with first end 6604*a* of horizontal beam 6602 and a second telescopic jack 664*b* that may be coupled with second end 6604*b* of horizontal beam 6602. In an exemplary embodiment, first telescopic jack 664*a* may include a first elongated housing 6640 that may extend along vertical axis 610, a first intermediate elongated member 6642 that may be mounted within first elongated housing 6640. In an exemplary embodiment, first intermediate elongated member 6642 may extend along vertical axis 610 and may be slidably moveable within first elongated housing 6640 along vertical axis 610. In an exemplary embodiment, first telescopic jack 664*a* may further include a first inner elongated member 6644 that may be mounted within first intermediate elongated member 6642, where first inner extendable elongated member 6644 may extend along vertical axis 610. First inner extendable elongated member 6644 may be slidably moveable within first intermediate elongated member 6642 along vertical axis 610. In an exemplary embodiment, a first end 66440 of first inner elongated member 6644 disposed within first intermediate elongated member 6642, a second opposing end 66442 of first inner elongated member 6644 coupled with first end 6604*a* of horizontal beam 6602.

In an exemplary embodiment, second telescopic jack 664*b* may be structurally similar with first telescopic jack 664*a*. Second telescopic jack 664*b* may include a second elongated housing 6640' that may extend along vertical axis 610, a second intermediate elongated member 6642' that may be mounted within second elongated housing 6640'. In an exemplary embodiment, second intermediate elongated member 6642' may extend along vertical axis 610 and may be slidably moveable within second elongated housing 6640' along vertical axis 610. In an exemplary embodiment, second telescopic jack 664*b* may further include a second inner elongated member 6644' that may be mounted within second intermediate elongated member 6642', where second inner extendable elongated member 6644' may extend along vertical axis 610. Second inner extendable elongated member 6644' may be slidably moveable within second intermediate elongated member 6642' along vertical axis 610. In an exemplary embodiment, a first end 66440' of second inner elongated member 6644' disposed within second intermediate elongated member 6642', a second opposing end 66442' of second inner elongated member 6644' coupled with second end 6604*b* of horizontal beam 6602.

In an exemplary embodiment, first telescopic jack 664*a* and second telescopic jack 664*b* may be mounted on a base 614 to actuate a linear motion of horizontal beam 6602 and all the other parts connected to horizontal beam 6602 along vertical axis 610 relative to base 614. In an exemplary embodiment, base 614 may include a trolley that may allow for moving ergonomic master console 60 on the floor. In an exemplary embodiment, first telescopic jack 664*a* and second telescopic jack 664*b* may be motorized and a respective electric motor within each of first telescopic jack 664*a* and second telescopic jack 664*b* may actuate their telescopic movements. Alternatively, telescopic movements of first telescopic jack 664*a* and second telescopic jack 664*b* may be actuated manually. In an exemplary embodiment, ergonomic adjustment mechanism 66 may further include a horizontal adjustment mechanism 662 that may be configured to move master robotic arms 62*a-b* along horizontal axis 612.

Figure 6D:
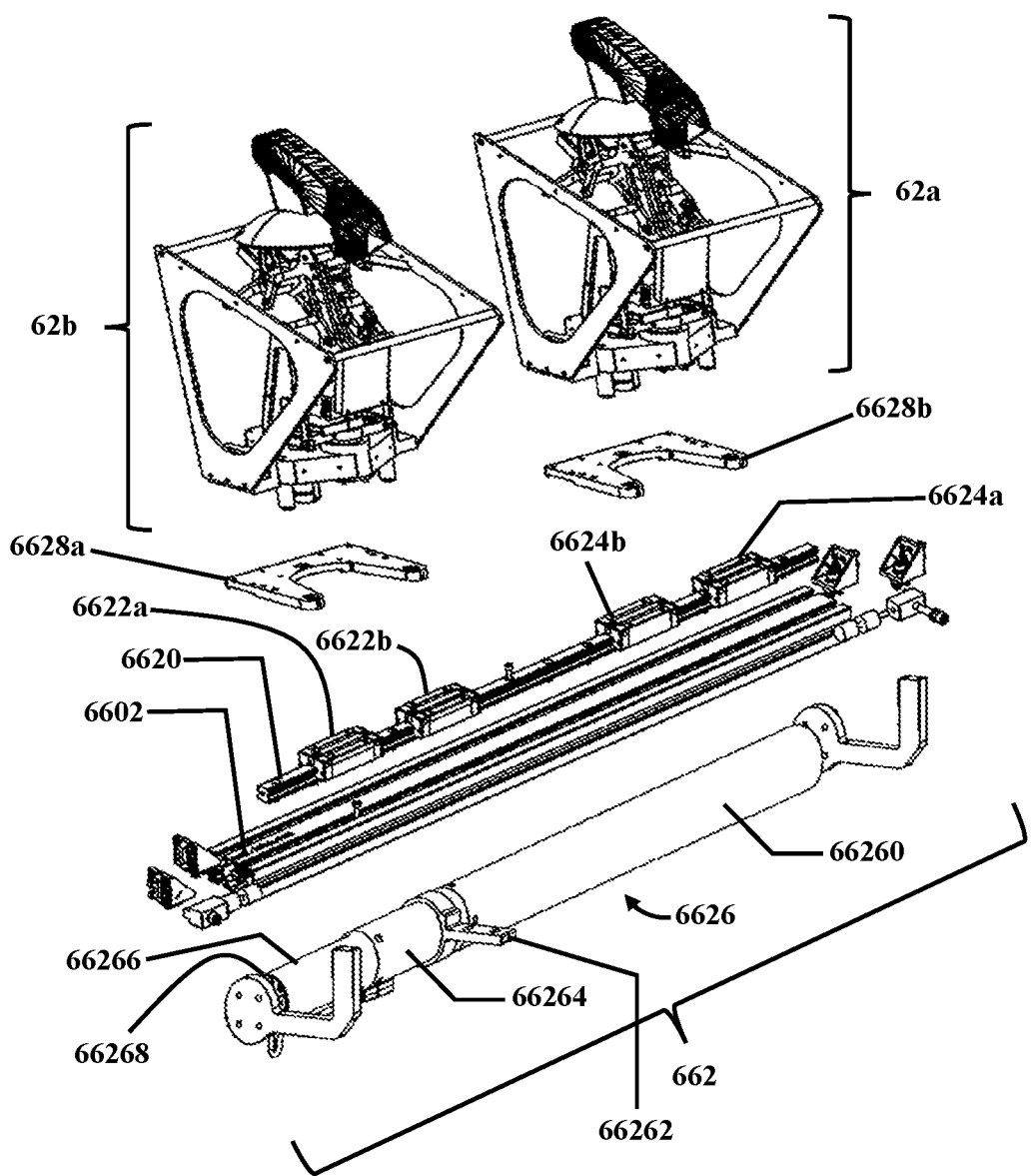
FIG. 6D illustrates an exploded perspective view of a horizontal adjustment mechanism, consistent with one or more exemplary embodiments of the present disclosure.

FIG. 6D illustrates an exploded perspective view of horizontal adjustment mechanism 662, consistent with one or more exemplary embodiments of the present disclosure. In an exemplary embodiment, horizontal adjustment mechanism 662 may include a horizontal sliding rail 6620 that may be parallel with and mounted on horizontal beam 6602. In an exemplary embodiment, master robotic arms 62*a-b* may be slidably mounted on sliding rail 6620, where master robotic arms 62*a-b* may be slidable on sliding rail 6620 along horizontal axis 612. In an exemplary embodiment, horizontal adjustment mechanism 662 may further include a first sliding wagon 6622*a* that may be slidably mounted on horizontal sliding rail 6620. First sliding wagon 6622*a* may be moveable along horizontal axis 612. First master robotic arm 62*a* may be mounted on first sliding wagon 6622*a*. In an exemplary embodiment, horizontal adjustment mechanism 662 may further include a first mounting platform 6628*a* on which first master robotic arm 62*a* may be mounted. In an exemplary embodiment, first mounting platform 6628*a* may be mounted on first sliding wagon 6622*a* and may function as a connecting member that facilitates connection of first master robotic arm 62*a* and first sliding wagon 6622*a*. In an exemplary embodiment, instead of one sliding wagon such as first sliding wagon 6622*a*, first mounting platform 6628*a* may be mounted on two sliding wagons, namely, first sliding wagon 6622*a* and another sliding wagon 6622*b* mounted on horizontal sliding rail 6620 adjacent first sliding wagon 6622*a*. Such utilization of an extra sliding wagon may be for obtaining a more stable horizontal movement of first master robotic arm 62*a* along horizontal axis 612.

In an exemplary embodiment, horizontal adjustment mechanism 662 may further include a second sliding wagon 6624*a* that may be slidably mounted on horizontal sliding rail 6620. Second sliding wagon 6624*a* may be moveable along horizontal axis 612, and second master robotic arm 62*b* may be mounted on second sliding wagon 6624*a*. In an exemplary embodiment, horizontal adjustment mechanism 662 may further include a second mounting platform 6628*b* on which second master robotic arm 62*b* may be mounted. In an exemplary embodiment, second mounting platform 6628*b* may be mounted on second sliding wagon 6624*a* and may function as a connecting member that facilitates connection of second master robotic arm 62*b* and second sliding wagon 6624*a*. In an exemplary embodiment, instead of one sliding wagon such as second sliding wagon 6624*a*, second mounting platform 6628*b* may be mounted on two sliding wagons, namely, second sliding wagon 6624*a* and another sliding wagon 6624*b* mounted on horizontal sliding rail 6620 adjacent second sliding wagon 6624*a*. Such utilization of an extra sliding wagon may be for obtaining a more stable horizontal movement of second master robotic arm 62*b* along horizontal axis 612.

In an exemplary embodiment, horizontal adjustment mechanism 662 may further include a linear actuator 6626 that may be coupled with first sliding wagon 6622*a* and second sliding wagon 6624*a*. In an exemplary embodiment, linear actuator 6626 may be configured to drive translational movements of first sliding wagon 6622*a* and second sliding wagon 6624*a* on horizontal sliding rail 6620 along horizontal axis 612.

In an exemplary embodiment, linear actuator 6626 may include a telescopic linear jack with an outer barrel 66260, where a distal end 66262 of outer barrel 66260 may be attached to first sliding wagon 6622. Linear actuator 6626 may further include an intermediate slidable member 66264 that may be disposed within outer barrel 66260. Intermediate slidable member 66264 may be fixedly attached to horizontal beam 6602 via a connecting member 66262, such that intermediate slidable member 66264 has no movements along horizontal axis 612 with respect to horizontal beam 6602. In an exemplary embodiment, linear actuator 6626 may further include an inner slidable rod 66266 that may be disposed within intermediate slidable member 66264. A distal end 66268 of inner slidable rod 66266 may be attached to first sliding wagon 6622*a* via a connecting member, such as a first L-shaped connecting member 662610. In an exemplary embodiment, first L-shaped connecting member 662610 may be connected to distal end 66268 of inner slidable rod 66266 from one end and may be connected to first mounting platform 6628*a* from the other end. A distal end 662612 of outer barrel 66260 may further be coupled with second sliding wagon 6624*a* via a connecting member, such as a second L-shaped connecting member 662614. In an exemplary embodiment, second L-shaped connecting member 662614 may be connected to distal end 662612 of outer barrel 66260 from one end and may be connected to second mounting platform 6628*b* from the other end.

In an exemplary embodiment, linear actuator 6626 may be configured to drive linear movements of first sliding wagon 6622 and second sliding wagon 6624 toward or away from each other along horizontal axis 612.

In an exemplary embodiment, hand-rest assembly 68 may include a flat surface 680, where a normal axis 6800 of flat surface 680 may be perpendicular to horizontal axis 612. Hand-rest assembly 68 may further include a first connecting rod 682*a* and a second connecting rod 682*b*. First connecting rod 682*a* may be a telescopic rod including two rods connected to each other and slidably moveable with respect to each other to allow for first connecting rod 682*a* to have an adjustable length as illustrated in FIG. 6B. Both rods of first connecting rod 682*a* are referred to by reference numeral 682*a* for simplicity. In an exemplary embodiment, a second connecting rod 682*b* may be structurally similar to first connecting rod 682*a* and both rods of second connecting rod 682*b* are referred to by reference numeral 682*b* for simplicity.

In an exemplary embodiment, a first end 6820*a* of first connecting rod 682*a* and a first end 6820*b* of second connecting rod 682*b* may be attached at either side of flat surface 680. In an exemplary embodiment, hand-rest assembly 68 may further include a first sliding rail 686*a* and a second sliding rail 686*b*. In an exemplary embodiment, hand-rest assembly 68 may further include a first sliding wagon 688*a* and a second sliding wagon 688*b*. First sliding wagon 688*a* may be mounted on first sliding rail 686*a* and second sliding wagon 688*b* may be mounted on second sliding rail 686*b*. In an exemplary embodiment, a second opposing end 6822*a* of first connecting rod 682*a* may be connected to first sliding wagon 688*a* and a second opposing end 6822*b* of second connecting rod 682*b* may be connected to second sliding wagon 688*b*. In an exemplary embodiment, first sliding wagon 688*a* may be slidable on first sliding rail 686*a* along a translational axis 6812. In an exemplary embodiment, translational axis may be perpendicular to both vertical axis 610 and horizontal axis 612. In an exemplary embodiment, second sliding wagon 688*b* may be slidable on second sliding rail 686*b* along translational axis 6812. Such sliding movements of first sliding rail 686*a* and second sliding wagon 688*b* along translational axis 6812 may allow for adjusting the position of hand-rest assembly along translational axis 6812.

In an exemplary embodiment, hand-rest assembly 68 may further include a height-adjustment actuator that may include a first linear actuator 6810*a* that may be connected between first end 6820*a* of first connecting rod 682*a* and flat surface 680. In an exemplary embodiment, linear actuator 6810*a* may be configured to drive a translational movement of flat surface 680 along vertical axis 610 with respect to first end 6820*a* of first connecting rod 682*a*.

In an exemplary embodiment, height-adjustment actuator of hand-rest assembly 68 may further include a second linear actuator 6810*b* that may be connected between second end 6820*b* of second connecting rod 682*b* and flat surface 680. In an exemplary embodiment, second linear actuator 6810*b* may be configured to drive a translational movement of flat surface 680 along vertical axis 610 with respect to second end 6820*b* of second connecting rod 682*b*.

In an exemplary embodiment, ergonomic adjustment mechanism 66 may include an upper frame 6606, on which master robotic arms 62*a-b*, horizontal adjustment mechanism 662, hand-rest adjustment mechanism, and parts of user-interface unit 64, such as monitor 640 may be mounted.

Figure 7:
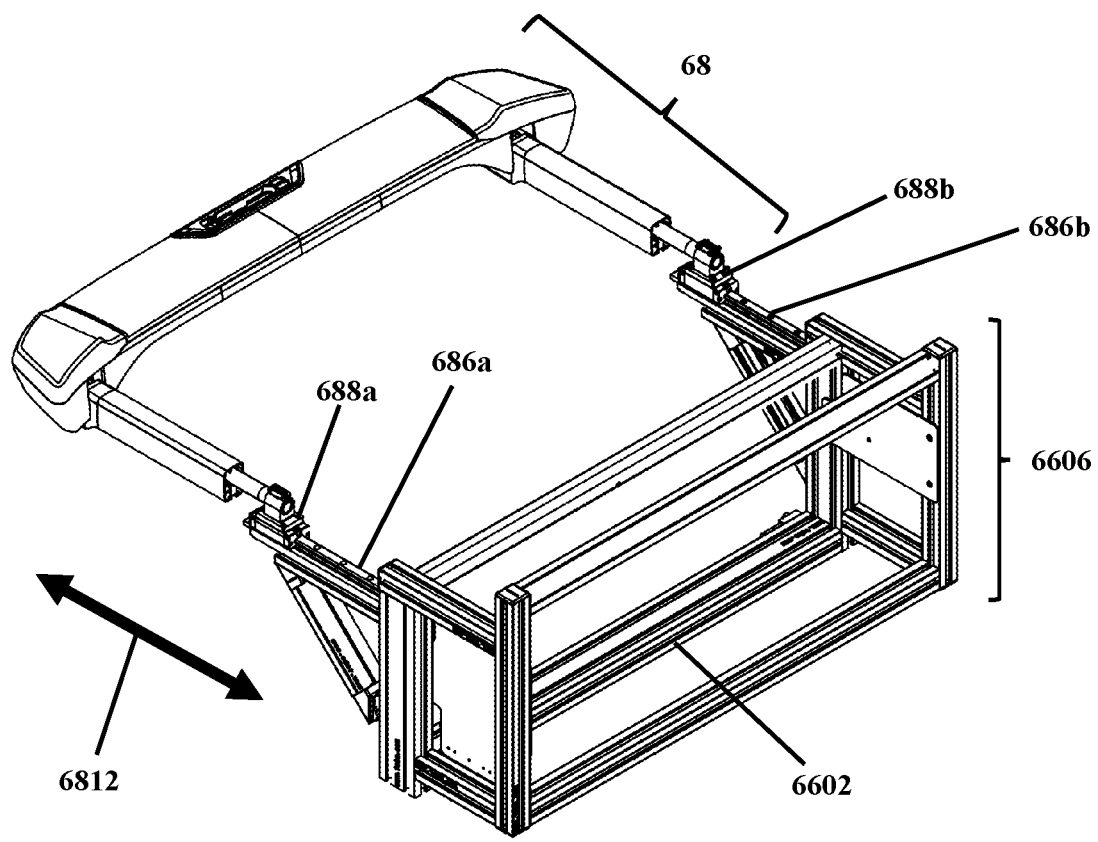
FIG. 7 illustrates a perspective view of an upper frame and a hand-rest assembly coupled to the upper frame, consistent with one or more exemplary embodiments of the present disclosure.

FIG. 7 illustrates a perspective view of upper frame 6606 and hand-rest assembly coupled to upper frame 6606, consistent with one or more exemplary embodiments of the present disclosure. In an exemplary embodiment, horizontal beam 6602 may form a lower edge of upper frame 6606 and the entire upper frame 6606 may be coupled to vertical adjustment mechanism 660. Referring to FIG. 6C, in an exemplary embodiment, second opposing end 66442 of first inner elongated member 6644 may be connected to an upper edge of upper frame 6606 via first connecting plate 6608*a* and second opposing end 66442' of second inner elongated member 6644' may be connected to an opposing upper edge of upper frame 6606 via second connecting plate 6608*b*. Such coupling between upper frame and vertical adjustment mechanism may allow for adjusting the height of anything mounted on upper frame along vertical axis.

In an exemplary embodiment, translational movements of first sliding wagon 688a on first sliding rail 686a and second sliding wagon 688b on second sliding rail 686b along translational axis 6812 may allow for adjusting the position of hand-rest assembly 68 along translational axis 6812 with respect to upper frame 6606.

Figure 8:
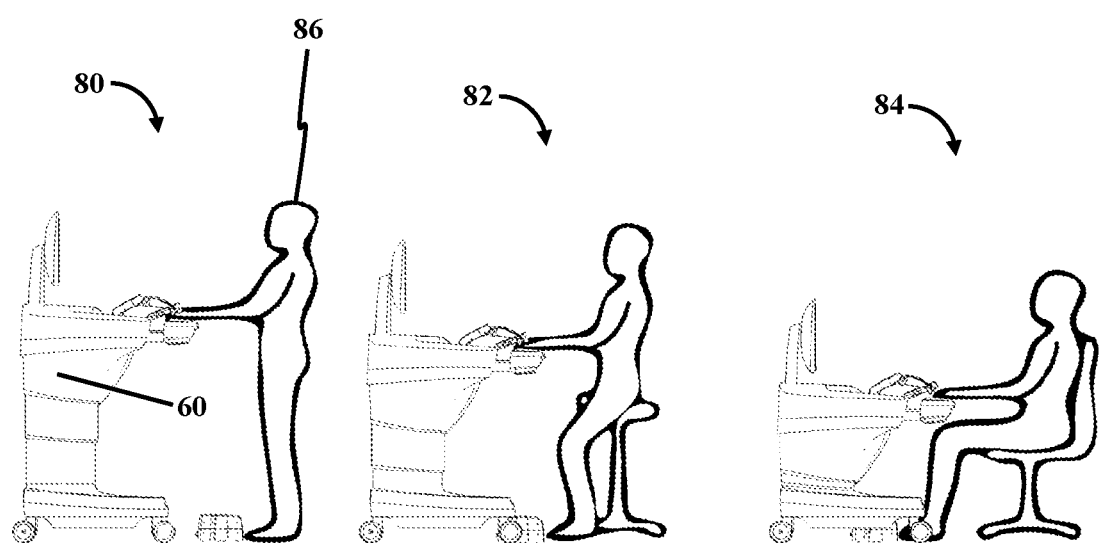
FIG. 8 illustrates an ergonomic master console at different positions adjusted by an ergonomic adjustment mechanism, consistent with one or more exemplary embodiments of the present disclosure.

In exemplary embodiments, ergonomic adjustment mechanism 66 of ergonomic master console 60 may allow for a surgeon 76 to perform remote surgery at various ergonomic positions of . . . . For example, FIG. 8 illustrates ergonomic master console 60 at different positions adjusted by ergonomic adjustment mechanism 66. In an exemplary embodiment, surgeon 86 (similar to surgeon 76??) may utilize ergonomic adjustment mechanism 66 to adjust ergonomic master console 60 at a standing position 80, a semi-sitting position 82, or a sitting position 84. Such ergonomic adjustment capabilities added to ergonomic master console 60 die to ergonomic adjustment mechanism 66 may significantly reduce fatigue for potential surgeons or users of an exemplary surgical device during long surgeries.

While the foregoing has described what are considered to be the exemplary embodiments, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of exemplary embodiments consistent with the present disclosure.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element. The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed is:

1. A robotic tele-surgery system, comprising:
 a slave robotic arm comprising three degrees of freedom, the three degrees of freedom comprising at least one of grasp, roll, pitch, and yaw;
 a master robotic arm comprising six degrees of freedom;
 a controller configured to establish a master-slave relationship between the slave robotic arm and the master robotic arm, wherein movement at the master robotic arm produces a proportional movement in the slave robotic arm; and
 an ergonomic adjustment mechanism comprising:
  a vertical adjustment mechanism configured to move the master robotic arm along a vertical axis, the vertical adjustment mechanism comprising:
   a horizontal beam extended along a horizontal axis between a first end and a second end, the horizontal axis perpendicular to the vertical axis; and
   a linear actuator coupled to the horizontal beam, the linear actuator configured to actuate a translational movement of the horizontal beam along the vertical axis; and
  a horizontal adjustment mechanism configured to move the master robotic arm along the horizontal axis, the horizontal adjustment mechanism comprising:
   a horizontal sliding rail mounted on the horizontal beam, the horizontal sliding rail parallel with the horizontal beam,
  wherein, the master robotic arm slidably mounted on the sliding rail, the master robotic arm slidable on the sliding rail along the horizontal axis.

2. The system of claim 1, wherein the linear actuator comprises:
 a first vertical track slidably coupled with the first end of the horizontal beam, the first vertical track configured to guide a linear translational movement of the first end along the vertical axis; and
 a second vertical track slidably coupled with the second end of the horizontal beam, the second vertical track configured to guide a linear translational movement of the second end along the vertical axis.

3. The system of claim 2, wherein the first vertical track comprises:

a first couple of parallel sliding rails extended along the vertical axis; and a first sliding wagon slidably mounted on the first couple of parallel sliding rails, the first sliding wagon moveable along the vertical axis, wherein, the first sliding wagon comprises a first bearing unit, the first bearing unit rotatably coupled with the first end of the horizontal beam.

4. The system of claim 3, wherein the second vertical track comprises:

a second couple of parallel sliding rails extending along the vertical axis; and a second sliding wagon slidably mounted on the second couple of parallel sliding rails, the second sliding wagon moveable along the vertical axis, wherein, the second sliding wagon comprises a second bearing unit, the second bearing unit rotatably coupled with the second end of the horizontal beam.

5. The system of claim 4, wherein the first sliding wagon further comprises a first lock, the first lock configured to lock the first sliding wagon in position at a desirable height along the vertical axis, the first lock comprising:

a locking screw; and a vertically extended locking plate comprising a plurality of stacked locking holes, each respective hole of the stacked locking holes positioned at a predetermined height along the vertical axis, each respective hole of the stacked locking holes configured to receive the locking screw therein.

6. The system of claim 1, wherein the horizontal adjustment mechanism further comprises a link radially extended outward from the horizontal beam between a proximal end and a distal end, the proximal end of the link attached to the horizontal beam, the horizontal sliding rail mounted on the distal end of the link.

7. The system of claim 1, wherein the horizontal sliding rail is rotatable with the horizontal beam about a main axis of the horizontal beam.

8. The system of claim 1, wherein the linear actuator comprises:

a first telescopic jack coupled with the first end of the horizontal beam, the first telescopic jack comprising:

a first elongated housing extended along the vertical axis;

a first intermediate elongated member mounted within the elongated housing, the first intermediate elongated member extended along the vertical axis, the first intermediate elongated member slidably moveable within the first elongated housing along the vertical axis; and a first inner elongated member mounted within the first intermediate elongated member, the first inner extendable elongated member extending along the vertical axis, the first inner extendable elongated member slidably moveable within the first intermediate elongated member along the vertical axis, a first end of the first inner elongated member disposed within the first intermediate elongated member, a second opposing end of the first inner elongated member coupled with the first end of the horizontal beam.

9. The system of claim 8, wherein the linear actuator comprises:

a second telescopic jack coupled with the second end of the horizontal beam, the second telescopic jack comprising:

a second elongated housing extending along the vertical axis;

a second intermediate elongated member mounted within the elongated housing, the second intermediate elongated member extended along the vertical axis, the second intermediate elongated member slidably moveable within the second elongated housing along the vertical axis; and a second inner elongated member mounted within the second intermediate elongated member, the second inner extendable elongated member extending along the vertical axis, the second inner extendable elongated member slidably moveable within the second intermediate elongated member along the vertical axis, a second end of the second inner elongated member disposed within the second intermediate elongated member, a second opposing end of the second inner elongated member coupled with the second end of the horizontal beam.

10. The system of claim 1, wherein the master robotic arm comprises a first master robotic arm and a second master robotic arm and wherein the horizontal adjustment mechanism further comprises:

a first sliding wagon slidably mounted on the horizontal sliding rail, the first sliding wagon moveable along the horizontal axis, the first master robotic arm mounted on the first sliding wagon; and a second sliding wagon slidably mounted on the horizontal sliding rail, the second sliding wagon moveable along the horizontal axis, the second master robotic arm mounted on the second sliding wagon.

11. The system of claim 10, wherein the horizontal adjustment mechanism further comprises a linear actuator coupled with the first sliding wagon and the second sliding wagon, the linear actuator configured to drive translational movements of the first sliding wagon and the second sliding wagon on the horizontal sliding rail along the horizontal axis.

12. The system of claim 11, wherein the linear actuator comprises a telescopic linear jack, the telescopic linear jack comprising:

an outer barrel, a distal end of the outer barrel attached to the first sliding wagon;

an intermediate slidable member disposed within the outer barrel, the intermediate slidable member fixedly attached to the horizontal beam with no movements along the horizontal axis with respect to the horizontal beam; and an inner slidable rod disposed within the intermediate slidable member, a distal end of the inner slidable rod attached to the second sliding wagon.

13. The system of claim 1, further comprising a hand-rest assembly, the hand-rest assembly comprising:

a flat surface, a normal axis of the flat surface perpendicular to the horizontal axis; and at least one connecting rod extending horizontally along a translational axis perpendicular to both the horizontal axis and the vertical axis, a first end of the at least one connecting rod attached to the flat surface, a second opposing end of the at least one connecting rod coupled to the ergonomic adjustment mechanism.

14. The system of claim 13, wherein the ergonomic adjustment mechanism further comprising:

at least one sliding rail extended along the translational axis; and at least one sliding wagon slidably coupled with the at least one sliding rail, the at least one sliding wagon moveable on the at least one sliding rail along the translational axis, the second opposing end of the at least one connecting rod attached to the at least one sliding wagon, the at least one connecting rod moveable with the at least one sliding wagon along the translational axis.

15. The system of claim 14, wherein:
the at least one connecting rod comprises two parallel connecting rods, each connecting rod of the two parallel connecting rods attached, from a first end of each connecting rod, to a corresponding edge at either end of the flat surface,
the at least one sliding rail comprises two parallel sliding rails, and
the at least one sliding wagon comprises two sliding wagons, each sliding wagon of the two sliding wagons slidably mounted on a corresponding sliding rail of the two parallel sliding rails, each connecting rod of the two parallel connecting rods coupled, from a second opposing end of each connecting rod, with a corresponding sliding wagon of the two sliding wagons.

16. The system of claim 13, wherein the hand-rest assembly further comprises:
a height-adjustment actuator comprising a linear actuator connected between the first end of the at least one connecting rod and the flat surface, the linear actuator configured to drive a translational movement of the flat surface along the vertical axis with respect to the first end of the at least one connecting rod.

\* \* \* \* \*